(12) United States Patent
Ingenito et al.

(10) Patent No.: US 8,361,484 B2
(45) Date of Patent: Jan. 29, 2013

(54) POLYMER SYSTEMS FOR LUNG VOLUME REDUCTION THERAPY

(75) Inventors: Edward P. Ingenito, North Quincy, MA (US); Alexander Schwarz, Brookline, MA (US); Larry W. Tsai, Boston, MA (US)

(73) Assignee: Aeris Therapeutics, Inc., Woburn, MA (US)

( * ) Notice: Subject to any disclaimer, the term of this patent is extended or adjusted under 35 U.S.C. 154(b) by 666 days.

(21) Appl. No.: 12/443,021

(22) PCT Filed: Sep. 27, 2007

(86) PCT No.: PCT/US2007/079504
§ 371 (c)(1),
(2), (4) Date: May 19, 2009

(87) PCT Pub. No.: WO2008/039827
PCT Pub. Date: Apr. 3, 2008

(65) Prior Publication Data
US 2010/0040538 A1 Feb. 18, 2010

Related U.S. Application Data

(60) Provisional application No. 60/847,328, filed on Sep. 26, 2006.

(51) Int. Cl.
*A61K 9/00* (2006.01)
(52) U.S. Cl. .......... 424/400; 424/78.08; 424/78.17; 424/78.18; 424/78.31
(58) Field of Classification Search .......... None
See application file for complete search history.

(56) References Cited

U.S. PATENT DOCUMENTS

| | | | |
|---|---|---|---|
| 6,350,527 B1 * | 2/2002 | Hubbell et al. | 428/473 |
| 6,514,528 B1 * | 2/2003 | Xia et al. | 424/464 |
| 6,610,043 B1 | 8/2003 | Ingenito | |
| 6,682,520 B2 | 1/2004 | Ingenito | |
| 7,070,809 B2 | 7/2006 | Goupil et al. | |
| 7,300,428 B2 | 11/2007 | Ingenito | |
| 7,468,350 B2 * | 12/2008 | Gong et al. | 514/1.1 |
| 2004/0038868 A1 | 2/2004 | Ingenito | |
| 2004/0047855 A1 | 3/2004 | Ingenito | |
| 2005/0244401 A1 | 11/2005 | Ingenito | |

OTHER PUBLICATIONS

International Search Report for PCT/US07/79504 mailed Sep. 2, 2008.

* cited by examiner

*Primary Examiner* — James Rogers
(74) *Attorney, Agent, or Firm* — Dana M. Gordon; Foley Hoag LLP

(57) ABSTRACT

One aspect of the invention relates to a hydrogel comprising a polymer comprising a plurality of pendent hydroxyl groups, a crosslinker, and a sclerosing agent. Another aspect of the invention relates to a method for reducing lung volume in a patient comprising the steps of advancing into a region of a patient's lung via said patient's trachea a multi-lumen catheter lumen through a bronchoscope; and co-administering, through the multi-lumen catheter, a first mixture comprising a first amount of a polymer containing a plurality of pendent hydroxyl groups; a second mixture comprising a second amount of a crosslinker; and a third mixture comprising a third amount of a sclerosing agent; thereby forming a hydrogel in said region. In certain embodiments, the compositions and methods described herein are intended for use in the treatment of patients with emphysema of the lung.

15 Claims, 3 Drawing Sheets

[A]

[B]

[A]

[B]

POLYMER SYSTEMS FOR LUNG VOLUME REDUCTION THERAPY

RELATED APPLICATIONS

This application is a §371 national stage application of Patent Cooperation Treaty Application number PCT/US07/79504, filed Sep. 26, 2007, which claims the benefit of priority to U.S. Provisional Patent Application Ser. No. 60/847,328, filed Sep. 26, 2006.

BACKGROUND OF THE INVENTION

Emphysema is a common form of chronic obstructive pulmonary disease (COPD) that affects between 1.5 and 2 million Americans, and 3 to 4 times that number of patients worldwide. [American Thoracic Society Consensus Committee "Standards for the diagnosis and care of patients with chronic obstructive pulmonary disease," *Am. J. Resp. Crit. Care Med.* 1995, 152, 78-83; and Pauwels, R., et al. "Global strategy for the diagnosis, management, and prevention of chronic obstructive pulmonary disease," *Am. J. Resp. Crit. Care Med.* 2001, 163, 1256-1271.] It is characterized by destruction of the small airways and lung parenchyma due to the release of enzymes from inflammatory cells in response to inhaled toxins. [Stockley, R. "Neutrophils and protease/anti-protease imbalance," *Am. J. Resp. Crit. Care Med.* 1999, 160, S49-S52.] Although this inflammatory process is usually initiated by cigarette smoking, once emphysema reaches an advanced stage, it tends to progress in an unrelenting fashion, even in the absence of continued smoking. [Rutgers, S. R., et al. "Ongoing airway inflammation inpatients with COPD who do not currently smoke," *Thorax* 2000, 55, 12-18.]

The class of enzymes that are responsible for producing tissue damage in emphysema are known as proteases. These enzymes are synthesized by inflammatory cells within the body and when released, they act to degrade the collagen and elastin fibers which provide mechanical integrity and elasticity to the lung. [Jeffery, P. "Structural and inflammatory changes in COPD: a comparison with asthma," *Thorax* 1998, 53, 129-136.] The structural changes that result from the action of these enzymes are irreversible, cumulative, and are associated with loss of lung function that eventually leaves patients with limited respiratory reserve and reduced functional capacity. [Spencer, S. et al. "Health status deterioration inpatients with chronic obstructive pulmonary disease," *Am. J. Resp. Crit. Care Med.* 2001, 163, 122-128; and Moy, M. L., et al. "Health-related quality of life improves following pulmonary rehabilitation and lung volume reduction surgery," *Chest* 1999, 115, 383-389.]

In contrast to other common forms of COPD, such as asthma and chronic bronchitis for which effective medical treatments exist, conventional medical treatment is of limited value in patients with emphysema. Although emphysema, astluna, and chronic bronchitis each cause chronic airflow obstruction, limit exercise capacity, and cause shortness of breath, the site and nature of the abnormalities in asthma and chronic bronchitis are fundamentally different from those of emphysema. In asthma and chronic bronchitis, airflow limitation is caused by airway narrowing due to smooth muscle constriction and mucus hyper-secretion. Pharmacologic agents that relax airway smooth muscle and loosen accumulated secretions are effective at improving breathing function and relieving symptoms. Agents that act in this way include beta-agonist and anti-cholinergic inhalers, oral theophylline preparations, leukotriene antagonists, steroids, and mucolytic drugs.

In contrast, airflow limitation in emphysema is not primarily due to airway narrowing or obstruction, but rather to loss of elastic recoil pressure as a consequence of tissue destruction. Loss of recoil pressure compromises the ability to fully exhale, and leads to hyper-inflation and gas trapping. Although bronchodilators, anti-inflammatory agents, and mucolytic agents are frequently prescribed for patients with emphysema, they are generally of limited utility since they are intended primarily for obstruction caused by airway disease. They do nothing to address the loss of elastic recoil that is principally responsible for airflow limitation in emphysema. [Barnes, P. "Chronic Obstructive Pulmonary Disease," *N. Engl. J. Med.* 2000, 343(4), 269-280.]

While pharmacologic treatments for advanced emphysema have been disappointing, a non-medical treatment of emphysema has recently emerged, which has demonstrated clinical efficacy. This treatment is lung volume reduction surgery (LVRS). [Flaherty, K. R. and F J. Martinez "Lung volume reduction surgery for emphysema," *Clin. Chest Med.* 2000, 21(4), 819-48.]

LVRS was originally proposed in the late 1950s by Dr. Otto Brantigan as a surgical remedy for emphysema. The concept arose from clinical observations which suggested that in emphysema the lung was "too large" for the rigid chest cavity, and that resection of lung tissue represented the best method of treatment since it would reduce lung size, allowing it to fit and function better within the chest. Initial experiences with LVRS confirmed that many patients benefited symptomatically and functionally from the procedure. Unfortunately, failure to provide objective outcome measures of improvement, coupled with a 16% operative mortality, led to the initial abandonment of LVRS.

LVRS was accepted for general clinical application in 1994 through the efforts of Dr. Joel Cooper, who applied more stringent pre-operative evaluation criteria and modern postoperative management schemes to emphysema patients. [Cooper, J. D., et al. "Bilateral pneumonectomy for chomic obstructive pulmonary disease," *J. Thorac. Cardiovasc. Surg.* 1995, 109, 106-119.] Cooper reported dramatic improvements in lung function and exercise capacity in a cohort of 20 patients with advanced emphysema who had undergone LVRS. There were no deaths at 90-day follow-up, and physiological and functional improvements were markedly better than had been achieved with medical therapy alone.

While less dramatic benefits have been reported by most other centers, LVRS has nevertheless proven to be effective for improving respiratory function and exercise capacity, relieving disabling symptoms of dyspnea, and improving quality of life in patients with advanced emphysema. [Gelb, A. F., et al. "Mechanism of short-term improvement in lung function after emphysema resection," *Am. J. Respir. Crit. Care Med.* 1996, 154, 945-51; Gelb, A. F., et al. "Serial lung function and elastic recoil 2 years after lung volume reduction surgery for emphysema," *Chest* 1998, 113(6), 1497-506; Criner, G. and G. E. D'Alonzo, Jr., "Lung volume reduction surgery: finding its role in the treatment of patients with severe COPD," *J. Am. Osteopath. Assoc.* 1998, 98(7), 371; Brenner, M., et al. "Lung volume reduction surgery for emphysema," *Chest* 1996, 110(1), 205-18; and Ingenito, E. P., et al. "Relationship between preoperative inspiratory lung resistance and the outcome of lung-volume-reduction surgery for emphysema," *N. Engl. J. Med.* 1998, 338, 1181-1185.] The benefits of volume reduction have been confirmed in numerous cohort studies, several recently-completed small randomized clinical trials, and the National Emphysema Treatment Trial (NETT). [Goodnight-White, S., et al. "Prospective randomized controlled trial comparing bilateral volume reduction surgery to medical therapy alone inpatients with severe emphysema," *Chest* 2000, 118(Suppl 4), 1028; Geddes, D., et al. "L-effects of lung volume reduction surgery inpatients with emphysema," *N. Eng. J. Med.* 2000, 343, 239-245; Pompeo, E., et al. "Reduction pneumoplasty versus respiratory rehabilitation in severe emphysema: a randomized study," *Ann. Thorac. Surg.* 2000, 2000(70), 948-954; and Fishman, A., et al. "A randomized trial comparing lung-volume-reduction surgery with medical therapy for severe emphysema," *N. Eng. J. Med.* 2003, 348(21): 2059-73.] On average, 75-80% of patients have experienced a beneficial clinical response to LVRS (generally defined as a 12% or greater improvement in FEV, at 3 month follow-up). The peak responses generally occur at between 3 and 6 months postoperatively, and improvement has lasted several years. [Cooper, J. D. and S. S. Lefrak "Lung-reduction surgery: 5 years on," *Lancet* 1999, 353(Suppl 1), 26-27; and Gelb, A. F., et al. "Lung function 4 years after lung volume reduction surgery for emphysema," *Chest* 1999, 116(6), 1608-15.] Results from NETT have further shown that in a subset of patients with emphysema, specifically those with upper lobe disease and reduced exercise capacity, mortality at 29 months is reduced.

Collectively, these data indicate that LVRS improves quality of life and exercise capacity in many patients, and reduces mortality in a smaller fraction of patients, with advanced emphysema. Unfortunately, NETT also demonstrated that the procedure is very expensive when considered in terms of Quality Adjusted Life Year outcomes, and confirmed that LVRS is associated with a 5-6% 90 day mortality. [Chatila, W., S. Furukawa, and G. J. Criner, "Acute respiratory failure after lung volume reduction surgery," *Am. J. Respir. Crit. Care Med.* 2000, 162, 1292-6; Cordova, F. C. and G. J. Criner, "Surgery for chronic obstructive pulmonary disease: the place for lung volume reduction and transplantation," Curr. Opin. Pulm. Med. 2001, 7(2), 93-104; Swanson, S. J., et al. "No-cut thoracoscopic lung placation: a new technique for lung volume reduction surgery," *J. Am. Coll. Surg.* 1997, 185(1), 25-32; Sema, D. L., et al "Survival after unilateral versus bilateral lung volume reduction surgery for emphysema," J. Thorac. Cardiovasc. Surg. 1999, 118(6), 1101-9; and Fishman, A., et al. "A randomized trial comparing lung-volume-reduction surgery with medical therapy for severe emphysema," *N. Engl. J. Med.* 2003, 348(21), 2059-73.] In addition, morbidity following LVRS is common (40-50%) and includes a high incidence of prolonged post-operative air-leaks, respiratory failure, pneumonia, cardiac arrhythmias, and gastrointestinal complications. Less invasive and less expensive alternatives that could produce the same physiological effect are desirable.

A hydrogel-based system for achieving lung volume reduction has been developed and tested, and its effectiveness confirmed in both healthy sheep, and sheep with experimental emphysema. [Ingenito, E. P., et al. "Bronchoscopic Lung Volume Reduction Using Tissue Engineering Principles," *Am. J. Respir. Crit. Care Med.* 2003, 167, 771-778.] This system uses a rapidly-polymerizing, fibrin-based hydrogel that can be delivered through a dual lumen catheter into the lung using a bronchoscope. The fibrin-based system effectively blocks collateral ventilation, inhibits surfactant function to promote collapse, and initiates a remodeling process that proceeds over a 4-6 week period. Treatment results in consistent, effective lung volume reduction. These studies have confirmed the safety and effectiveness of using fibrin-based hydrogels in the lung to achieve volume reduction therapy.

While the treatment using fibrin-based hydrogels resulted in effective lung volume reduction, the use of biologically derived proteins is fraught with uncertainties due, e.g., to the danger of viral contamination. Although fibrinogen is purified under strict controls and the purification utilizes various viral reduction steps, a small risk of viral contamination always remains. Furthermore, the incidence of bovine spongiform encephalopathy (BSE) dramatically reduced the potential donor pool of donated blood used as source for fibrinogen. Thus, finding adequate fibrinogen to meet clinical demands may be problematic.

Therefore, a need exists for alternative hydrogel systems for LVRT that are easily sourced in large quantity and carry no or negligible viral contamination risk.

SUMMARY OF THE INVENTION

One aspect of the invention relates to a hydrogel comprising a polymer comprising a plurality of pendent hydroxyl groups, a crosslinker, and a sclerosing agent. In certain embodiments the invention relates to a three-dimensional matrix of a hydrogel formed by chemically linking polymer chains with pendent hydroxy groups using a boron compound.

Another aspect of the invention relates to a method for reducing lung volume in a patient comprising the steps of advancing into a region of a patient's lung via said patient's trachea a multi-lumen catheter lumen through a bronchoscope; and co-administering, through the multi-lumen catheter, a first mixture comprising a first amount of a polymer containing a plurality of pendent hydroxyl groups; a second mixture comprising a second amount of a crosslinker; a third mixture comprising a third amount of a sclerosing agent and optionally a fourth amount of a polyanion; thereby forming a hydrogel in said region. In certain embodiments, the compositions and methods described herein are intended for use in the treatment of patients with emphysema of the lung.

DETAILED DESCRIPTION OF THE INVENTION

Figure 1:
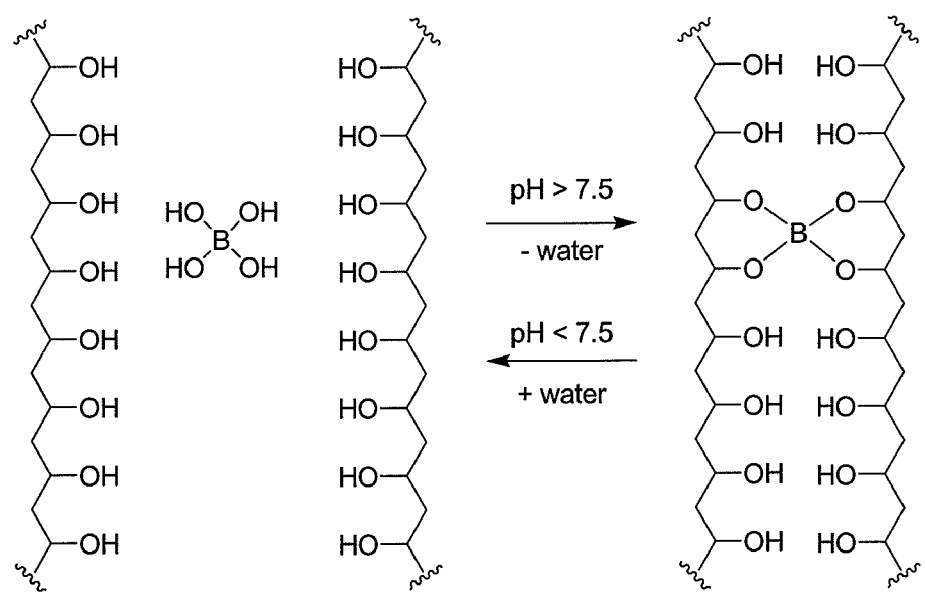
FIG. 1 depicts crosslinking of polyvinyl alcohol (PVA) with borate.

One aspect of the invention relates to compositions and methods for treatment of patients with advanced emphysema. In certain embodiments, the specific treatment described herein is a system for achieving lung volume reduction therapy through the introduction of a hydrogel, in which hydrogel precursors are injected into the lung as liquids, and polymerize in situ to form hydrogels. Delivery of the liquid precursors of the hydrogel may follow an initial pretreatment designed to prime the treatment area by causing collapse and/or by removing the surface lining cells of the treatment area. However, certain hydrogels can, by themselves, provide this function and do not require pretreatment.

The hydrogel serves several key functions that are beneficial for promoting lung volume reduction: it blocks collateral ventilation by coating the interstices of the lung surface, a step that prevents rapid re-inflation of the treatment area; it helps to ensure that reagents remain localized to the treatment area, since upon polymerization, the gel becomes trapped in the small airways and alveoli of the lung, preventing flow beyond the intended treatment site; and it fills the treatment area, displacing air and forming a bridge between adjacent regions of lung tissue.

If the polymer is biodegradable or resorbable, the surrounding tissues respond to the degrading hydrogel and cells start growing into the hydrogel. The biological matrix deposited by these cells links the adjacent areas of tissue providing a permanent tissue bridge that ensures a durable volume reduction response.

To be effective as a volume reducing agent in the lung, the precursors of the hydrogels must have sufficiently fast polymerization kinetics and physical properties that allow for endoscopic delivery. The formed hydrogels must have favorable biocompatibility profiles, show rapid polymerization, and have mechanical properties such that following polymerization the firmness of the gel does not mechanically injure adjacent soft lung tissues. Further, the pre-polymerized hydrogel components must have a viscosity that will allow them to be injected through a small-bore catheter. In addition, if degradable or resorbable, hydrogels must have acceptable pharmacokinetic degradation profiles in vivo. Hydrogels possessing some or all of these features should be satisfactory for achieving lung volume reduction therapy using a bronchoscopic approach.

This application describes hydrogels that possess some or all of these properties. In addition, the hydrogels of the invention show superior properties to the known LVRT compositions because of improved tissue adhesion; the hydrogels of the invention have minimal seepage and are self-healing (i.e., substantially less cracks or breaks are formed in the solidified mass). An additional improvement of the invention is that the hydrogels of the invention can be administered as a foam containing oxygen.

DEFINITIONS. For convenience, before further description of the present invention, certain terms employed in the specification, examples, and appended claims are collected here. These definitions should be read in light of the remainder of the disclosure and as understood by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 80 or fewer carbon atoms in its backbone (e.g., $C_1$-$C_{80}$ for straight chain, $C_3$-$C_{80}$ for branched chain), and alternatively, about 30 or fewer. Likewise, cycloalkyls have from about 3 to about 10 carbon atoms in their ring structure, and alternatively about 5, 6 or 7 carbons in the ring structure. As used herein, "fluoroalkyl" denotes an alkyl where one or more hydrogens have been replaced with fluorines; "perfluoroalkyl" denotes an alkyl where all the hydrogens have been replaced with fluorines.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "boroxine" is art-recognized and as used herein refers to a species such as that shown below; for example, when R57 represents alkyl the compound is referred to as an alkyl boroxine. A boroxine is represented by the general formula:

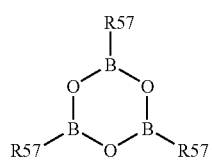

wherein R57 is independently hydroxyl, alkyl, cycloalkyl, aryl, aralkyl, alkyloxy, cycloalkyloxy, aryloxy or aralkyloxy.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

For purposes of this invention, the chemical elements are identified in accordance with the Periodic Table of the Elements, CAS version, "Handbook of Chemistry and Physics", 67th Ed., 1986-87, inside cover.

The term "contrast-enhancing" refers to materials capable of being monitored during injection into a mammalian subject by methods for monitoring and detecting such materials, for example by radiography or fluoroscopy. An example of a contrast-enhancing agent is a radiopaque material. Contrast-enhancing agents including radiopaque materials may be either water soluble or water insoluble. Examples of water soluble radiopaque materials include metrizamide, iopamidol, iothalamate sodium, iodomide sodium, and meglumine. Examples of water insoluble radiopaque materials include metals and metal oxides such as gold, titanium, silver, stainless steel, oxides thereof, aluminum oxide, zirconium oxide, etc.

As used herein, the term "polymer" means a molecule, formed by the chemical union of two or more oligomer units. The chemical units are normally linked together by covalent linkages. The two or more combining units in a polymer can be all the same, in which case the polymer is referred to as a homopolymer. They can be also be different and, thus, the polymer will be a combination of the different units. These polymers are referred to as copolymers.

Therefore, as used herein "a polymer with a plurality of pendent hydroxyl groups" is a polymer, as discussed above, wherein hydroxyl groups are directly bonded to the backbone of the polymer, or are connected to the polymer backbone via a tether, or both.

The term "hydrogels," as used herein, refers to a network of polymer chains that are water-soluble, sometimes found as a colloidal gel in which water is the dispersion medium.

In other words, hydrogels are two- or multicomponent systems consisting of a three-dimensional network of polymer chains and water that fills the space between the macromolecules. Hydrogels are composed of superabsorbent natural or synthetic polymers. As used herein, hydrogels are three dimensional networks formed by cross-linked chemical subunits which upon cross-linking trap a substantial amount of water, such that the majority of their mass (typically greater than about 80%) is contributed by the entrapped water.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

"Alginic acid" as used here in is a naturally occurring hydrophilic colloidal polysaccharide obtained from the various species of brown seaweed (Phaeophyceae). It occurs in white to yellowish brown filamentous, grainy, granular or powdered forms. It is a linear copolymer consisting mainly of residues of β-1,4-linked D-mannuronic acid and α-1,4-linked L-glucuronic acid. These monomers are often arranged in homopolymeric blocks separated by regions approximating an alternating sequence of the two acid monomers, as shown below:

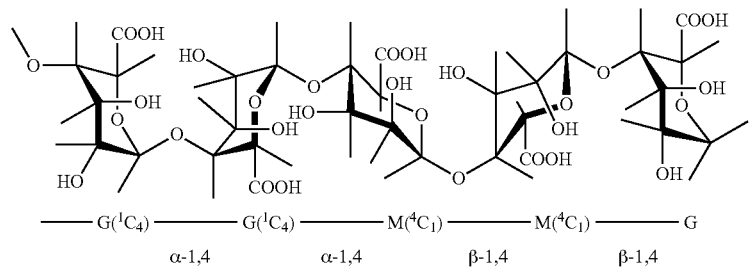

The formula weight of the structural unit is 176.13 (theoretical; 200 is the actual average). The formula weight of the macromolecule ranges from about 10,000 to about 600,000 (typical average).

"Sodium alginate" and "potassium alginate" are salts of alginic acid. For example, "potassium alginate" is shown below:

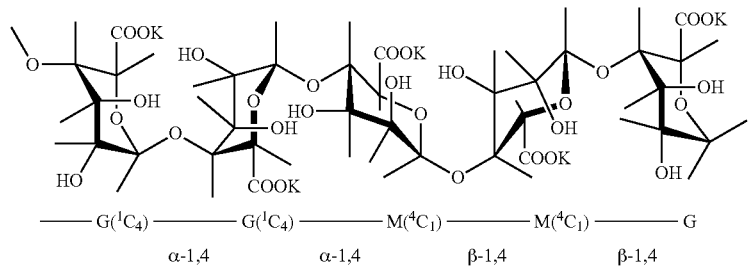

"Gellan gum" is a high molecular weight polysaccharide gum produced by a pure culture fermentation of a carbohydrate by *Pseudomonas elodea*, purified by recovery with isopropyl alcohol, dried, and milled. The high molecular weight polysaccharide is principally composed of a tetrasaccharide repeating unit of one rhamnose, one glucuronic acid, and two glucose units, and is substituted with acyl (glyceryl and acetyl) groups as the O-glycosidically-linked esters. The glucuronic acid is neutralized to a mixed potassium, sodium, calcium, and magnesium salt. It usually contains a small amount of nitrogen containing compounds resulting from the fermentation procedures. It has a formula weight of about 500,000. "Sodium gellan" and "potassium gellan" are salts of gellan gum.

Carboxymethylcellulose (CMC) is a polymer derived from natural cellulose. Unlike cellulose, CMC is highly water-soluble. The CMC structure is based on the β-(1-4)-D-glucopyranose polymer of cellulose. Different preparations may have different degrees of substitution, but it is generally in the range of about 0.6 to about 0.95 derivatives per monomer unit, as shown below:

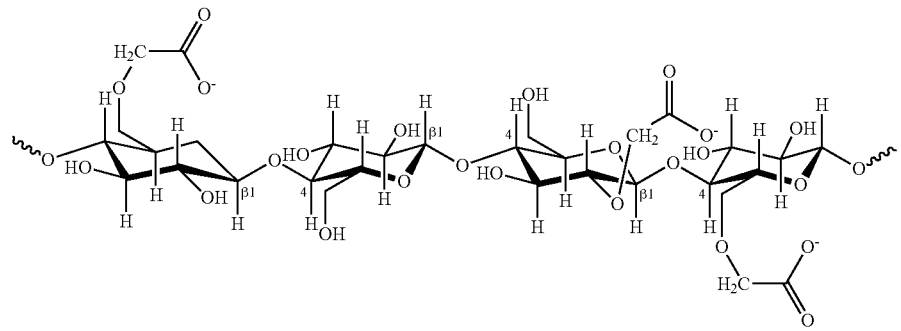

CMC molecules are somewhat shorter, on average, than native cellulose with uneven derivatization giving areas of high and low substitution. This substitution is mostly 2-O— and 6-O-linked, followed in order of importance by 2,6-di-O— then 3-O—, 3,6-di-O—, 2,3-di-O— lastly 2,3,6-tri-O-linked. It appears that the substitution process is a slightly cooperative (within residues) rather than random process giving slightly higher than expected unsubstituted and trisubstituted areas. CMC molecules are most extended (rod-like) at low concentrations but at higher concentrations the molecules overlap and coil up and then, at high concentrations, entangle to become a thermoreversible gel. Increasing ionic strength and reducing pH both decrease the viscosity as they cause the polymer to become more coiled. The average chain length and degree of substitution are of great importance; the more-hydrophobic lower substituted CMCs are thixotropic but more-extended higher substituted CMCs are pseudoplastic. At low pH, CMC may form cross-links through lactonization between carboxylic acid and free hydroxyl groups.

"Poly vinyl alcohol" (PVA) is a water soluble polymer synthesized by hydrolysis of a poly vinyl ester such as the acetate and used for preparation of fibers. PVA is a thermoplastic that is produced from full or partial hydrolysis of vinyl ester such as vinyl acetate resulting in the replacement of some or all of the acetyl groups with hydroxyl groups. For example:

In certain embodiments polyvinyl alcohol (PVA) is a synthetic resin produced by polymerisation of vinyl acetate (VAM) followed by hydrolysis of the polyvinyl acetate (PVAc) polymer. The degree of polymerisation determines the molecular weight and viscosity in solution. The degree of hydrolysis (saponification) signifies the extent of conversion of the polyvinyl acetate to the polyvinyl alcohol For example n (degree of hydrolysis) may be in the range of about 68.2 to about 99.8 mol. % and the MW (weight average molecular weight) may range from about 10,000 to about 190,000.

Hyaluronic acid (HA) is a polymer composed of repeating dimeric units of glucuronic acid and N-acetyl glucosamine. It may be of extremely high molecular weight (up to several million daltons) and forms the core of complex proteoglycan aggregates found in extracellular matrix. HA is comprised of linear, unbranching, polyanionic disaccharide units consisting of glucuronic acid (GlcUA) an N-acetyl glucosamine (GlcNAc) joined alternately by β-1-3 and β-1-4 glycosidic bonds (see below). It is a member of the glycosaminoglycan family which includes chondroitin sulphate, dermatin sulphate and heparan sulphate. Unlike other members of this family, it is not found covalently bound to proteins.

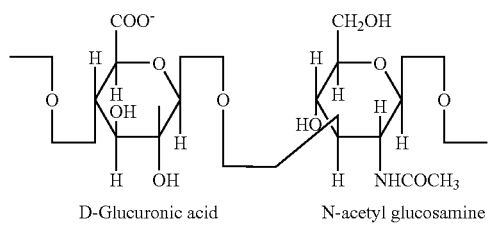

D-Glucuronic acid      N-acetyl glucosamine

When incorporated into a neutral aqueous solution hydrogen bond formation occurs between water molecules and adjacent carboxyl and N-acetyl groups. This imparts a conformational stiffness to the polymer, which limits its flexibility. The hydrogen bond formation results in the unique water-binding and retention capacity of the polymer. It also follows that the water-binding capacity is directly related to the molecular weight of the molecule. Up to six liters of water may be bound per gram of HA.

HA solutions are characteristically viscoelastic and pseudoplastic. This rheology is found even in very dilute solutions of the polymer where very viscous gels are formed. The viscoelastic property of HA solutions which is important in its use as a biomaterial is controlled by the concentration and molecular weight of the HA chains. The molecular weight of HA from different sources is polydisperse and highly variable ranging from 104 to $10^7$ Da. The extrusion of HA through the cell membrane as it is produced permits unconstrained polymer elongation and hence a very high molecular weight molecule.

HYDROGELS. Hydrogels suitable for use preferably crosslink upon the addition of the crosslinker, i.e., without the need for a separate energy source. Such systems allow good control of the crosslinking process, because gelation does not occur until the mixing of the two solutions takes place. If desired, polymer solutions may contain dyes or other means for visualizing the hydrogel. The crosslinkable solutions also may contain a bioactive drug or therapeutic compound that is entrapped in the resulting hydrogel, so that the hydrogel becomes a drug delivery vehicle.

Properties of the hydrogel system, other than crosslinkability, preferably should be selected on the basis of exhibited biocompatibility and lack of toxicity. Additionally, the hydrogel precursor solutions should not contain harmful or toxic solvents. Preferably, the hydrogel precursors are substantially soluble in water to allow application in a physiologically compatible solution, such as buffered isotonic saline. It is also preferable that the hydrogel be biodegradable, so that it does not have to be retrieved from the body. Biodegradability, as used herein, refers to the predictable disintegration of the hydrogel into molecules small enough to be metabolized or excreted under normal physiological conditions.

One aspect of the invention relates to a hydrogel formed by the polymerization of at least one monomer which upon polymerization forms a polymer with one or more pendant hydroxyl groups per monomer unit. Vinyl acetate is an example, which upon polymerization and subsequent hydrolysis forms poly(vinylalcohol). Certain saccharides are also examples of monomers with this characteristic. In certain embodiments, the monomers may be copolymerized with a copolymerizable monomer to form a copolymer with pendant hydroxyl groups. Glucomannan, which is a polymer of mannose and glucose, is an example of such a copolymer.

BORON CROSSLINKERS. The present invention makes use of the ability of boron to bond to polymers containing pendant hydroxyl groups. A variety of boron compounds can be used as crosslinkers in the present invention. In certain embodiments, the crosslinker of the invention is selected from the group consisting of boric acid, borates, boronic acids, boronates and boroxines. In certain embodiments, the reaction is performed at a slightly alkaline pH and reveres slowly at physiological pH.

SCLEROSING AGENTS. The present invention also makes use of compounds which damage lung tissue. For example, in some embodiments a sclerosing agent can be used as part of the administered composition. In some embodiments, the sclerosing agent may be administered alone; or it may be administered separately at the same time as, before, or after administration of cross-linkers and polymers of the present invention. The sclerosing agent can serve to bring about scar tissue formation, and/or fibroblast proliferation, and/or collagen synthesis, facilitating sealing of regions of damaged lung tissue. Sclerosing agents that may be used in the present invention include polycations, water soluble peroxides, and the like. When a polycation is used, a polyanion may also be used; cytotoxicity of the polycation can be "tuned" by changing the amount of polycation and amount of polyanion used. Polyelectrolytes of the invention are discussed in more detail in the following section. Other agents and/or methods for damaging lung tissue may also be used in the practice of the present invention.

POLYELECTROLYTES. Polyelectrolytes are polymers whose repeat units bear an electrolyte group. These groups can dissociate in aqueous solutions (e.g., water), making some or all of the polymer repeat units charged. After such electrolytic dissociation, the polymeric species is called a polycation or polyanion, if its repeat units are positively or negatively charged, respectively. A polyelectrolyte that gives rise to a polymer bearing both positive and negative charges after electrolytic dissociation is called an amphoteric polyelectrolyte, or polyampholyte. We use the generic term "polyion" or "polyionic" to refer to electrolytically dissociated polymers of unspecified charge. The ions that dissociate from the polymer are known as counterions.

Polyions can be further divided into 'weak' and 'strong' types. A 'strong' polyion is one which completely retains its charge in solution for most reasonable pH values. A 'weak' polyion is one whose charge can be substantially changed by proton transfer to or from the aqueous medium, in the pH range of ~2 to ~10. Thus, weak polyions may not be fully charged in solution and their fractional charge can be modified by changing the solution pH.

Polycations can be any of a variety of compounds having multiple positive charges and a net positive charge. For instance, the polycation can contain monomer units that are charge positive, charge neutral, or charge negative, however, the net charge of the polymer must be positive. Suitable classes of polycations may include, without limitation, natural or synthetic polymers, natural or synthetic polypeptides or non-peptides, and homopolymers or heteropolymers. Other classes of polycations can include polycationic carbohydrates, polycationic synthetic polymers, polycationic small synthetic organic amines, inorganic multivalent cations, cationic lipids, and synthetic viral particles. Polycations can also be divided into classes based on functional groups (e.g., polyamines and polyimines), molecular weight, or degree of interconnection between repeat units (e.g., linear or branched polymers). In some instances, a polycation may fall under two or more different classes of polycations. Polycations may be present alone, or as a mixture of two or more different polycations.

Polycations may exist as naturally occurring polypeptides or proteins such as protamines and histones. Protamines are a specialized class of strongly basic polypeptides which contain multiple positively charged amino acids, usually arginine. Histones are a class of compounds that include small DNA-binding proteins which are usually associated with chromatin and have a high proportion of positively charged amino acids, such as lysine and arginine. Other examples of naturally occurring polycations include granzyme, β-trypsin, and human serum albumin.

Polycations may fall under the class of synthetic polypeptides, also known as polyamino acids. A synthetic polypeptide may be a homopolymer of one of the positively charged (i.e., basic) amino acids such as lysine, arginine, or histidine, or a heteropolymer of two or more positively charged amino acids. In some embodiments, the polycation may be poly-D-lysine, poly-L-lysine, poly-DL-lysine, polyarginine, and polyhistidine. In addition, the polymer may comprise one or more positively charged non-standard amino acids such as ornithine, 5-hydroxylysine and the like. Or, the polypeptide may be functionalized with other groups, such as poly(γ-benzyl-L-glutamate). Furthermore, the polymer may include a mixture of positive, neutral and negative amino acids so long as the net charge is positive. Any or a combination of these or other amino acids can be polymerized into linear, branched, or cross-linked chains to generate polycationic polypeptides which are useful components in the compositions and methods described herein. Such polycationic polypeptides may contain at least 5 amino acid residues, at least 20 amino acid residues, at least 50 amino acid residues, at least 100 amino acid residues, at least 200 amino acid residues, at least 300 amino acid residues, at least 500 amino acid residues, at least 750 amino acids, at least 1000 amino acids, or more (e.g., from about 20 to about 150 amino acid residues, from about 50 to about 150 amino acid residues, or from about 50 to about 100 amino acid residues, etc.). Synthetic polypeptides can be produced by methods known to those of ordinary skill in the art, for example, by chemical synthetic methods or recombinant methods.

Polycations may occur as natural or synthetic organic polymers (i.e., non-peptides) bearing multiple charges. For instance, in some embodiments, polycations may include polyamines such as poly(ethylene imine), polypropylene imine (PPI), polyaniline, spermine, and spermidine. In other embodiments, polycations can be found as polyamides such as polyamide (Nylon), poly(ε-caprolactam) (Nylon 6), poly(hexamethylene adipamide) (Nylon 66), polyisocyanate, and polylactam. Polycations can also include polyimides such as polyimide, polynitrile, and poly(pyromellitimide-1,4-diphenyl ether) (Kapton); vinyl polymers such as polyacrylamide, poly(2-vinyl pyridine), poly(N-vinylpyrrolidone), poly(methylcyanoacrylate), poly(ethylcyanoacrylate), poly(butylcyanoacrylate), poly(isobutylcyanoacrylate), and poly(isohexylcynaoacrylate); polyaramides such as poly(imino-1,3-phenylene iminoisophthaloyl) and poly(imino-1,4-phenylene iminoterephthaloyl); polyheteroaromatic compounds such as polybenzimidazole (PBI), polybenzobisoxazole (PBO), polybenzobisthiazole (PBT); polyheterocyclic compounds such as polypyrrole; polysaccharides such as chitosan and N-trimethylchitosan; polyureas; and polyurethanes.

Additional examples of polycations include cationized gelatins, DNA binding proteins, non-histone chromosomal proteins, coat proteins from DNA viruses such as [phi]X174, myelin basic protein, low molecular weight glycopeptides, cationic amphiphilic alpha-helical oligopeptides having a repeating sequence, polybrene, putrescine, cadaverine, hexamine, polyvinylimidazolinium (PVA), and diethyl amino ethyl dextran (DEAD).

In some instances, natural or synthetic organic polymers that are not typically polycationic can be modified (i.e., derivatized) by introducing charges into the polymer to form polycationic polymers. In some cases, charges are introduced into a polymer by adding cationic and/or polycationic substituents. For example, diethylaminoethyl (DEAE) is a cation that can be introduced into a variety of polymers such as polyacrylate and polyimine-based polymers. Other cationic and/or polycationic substituents may also be used. Examples of polymers that can be modified to contain cationic and/or polycationic substituents include vinyl polymers such as poly(acrylic acid), poly(methyl acrylate), polyacrylonitrile, poly(p-methyl styrene), polystyrene, poly(vinyl acetate), poly(vinyl alcohol), poly(vinyl benzoate), and poly(vinyl chloride); vinylidene polymers such as poly(vinylidene chloride) (PVDC), polyisobutylene, and poly(methyl styrene); diene polymers such as 1,2-polybutadiene, 1,4-polybutadiene, 1,4-polychloroprene, and 1,4-polyisoprene; polyolefin polymers such as poly(butene-1), polyethylene, poly(n-pentene-2), poly(n-pentene-1), and polypropylene; polyesters such as polybutylene-terephthalate, poly(c-caprolactone), polycarbonate, polethylene-terephthalate, polyhydroxybutyrate, and polylactone; polyethers such as poly(ethylene glycol), poly(methylene oxide), poly(p-phenylene oxide), poly(propylene oxide), and poly(tetramethylene oxide); polyketones such as polyetheretherketone; polyaromatic compounds such as poly(p-phenylyene vinylene) and poly(p-phenylene); polysaccharides such as amylose, cellulose, alginate, and dextran; cellulose esters such as cellulose acetate, cellulose nitrate, and hydroxypropylcellulose; polyalkynes such as polyacetylene; polysulfide polymers such as polysulfide (thiokol) and poly(p-phenylene sulfide); polyheterocyclic compounds such as polythiphene; phenolic polymers such as phenol-formaldehyde; polysiloxanes such as polydiethylsiloxane (PDES), polydimethylsiloxane (PDMS), polydiphenylsiloxane (PDPS), and polymethylphenylsiloxane (PMPS); polyacetals; epoxys; polysulfurs; combinations thereof, and the like.

In some embodiments, a polycation composition may include inorganic polymers. Inorganic polymers can also be modified by introducing charges into the polymer to form polycationic polymers. Non-limiting examples of inorganic polymers include polyphosphate, polyphosphonate, polysilane, polysilazane, and polysiloxane.

In other embodiments, a polycationic composition can comprise a polyion that has been modified to reduce its overall charge.

Polycations can be classified as homopolymers, polymers having single repeating units, or heteropolymers, polymers having two or more different repeat units (e.g., copolymers and terpolymers). Polycationic heteropolymers can include one or more different repeat units bearing a positive charge. For instance, one repeat unit of the heteropolymer may be cationic, and the other repeat unit may or may not be cationic. Polymers that are heteropolymers can be further divided into random copolymers, block copolymers, graft copolymers, and alternating copolymers. Different portions (i.e., segments) of the polymer may allow the polymer to have different functionalities; for example, particular portions of the polymer may be used to increase or reduce interaction of the polymer with certain components in the body (e.g., blood components) when administered to a target area.

Random copolymers are copolymers comprising alternating segments of two or more monomeric units of random length, including single molecules. For example, a random copolymer having repeat units A and B may form a polymer such as ABBAAABABBA. Random copolymers can be formed, for instance, by the copolymerization of two monomers in the presence of a free-radical initiator. Polycationic random copolymers can be formed from one or more types of cationic monomers.

Block copolymers are copolymers with chains composed of homopolymeric chains which are linked together. These blocks (or segments) can be either regularly alternating or random. For example, a block copolymer having repeat units A and B may form a regularly alternating polymer such as AABBAABBAABB, or a randomly alternating polymer such as AAAABBBAABBB. Polycationic block copolymers can be formed from one or more types of cationic segments. In one embodiment, a polycationic block copolymer comprises a cationic segment and a hydrophilic segment. In another embodiment, a polycationic block copolymer comprises a cationic segment and a hydrophobic segment. In another embodiment, a polycationic polymer compositions two or more cationic segments.

Graft copolymers are polymers whose configuration consists of many homopolymeric branches joined or grafted to another homopolymer. For example, a graft copolymer having repeat units A and B may form a polymer such as AAAAAABBBBB. Polycationic graft copolymers can be formed from one or more types of cationic homopolymers.

Alternating copolymers are copolymers comprising alternating monomeric units. For example, an alternating copolymer having repeat units A and B may form a polymer such as ABABABABABAB. Polycationic alternating polymers can be formed from one or more types of cationic monomeric units.

Polycationic polymers may have different degrees of interconnection between repeat units. In one embodiment, a polycationic polymer is a linear polymer, a polymer composed of a single continuous chain of repeat units. In another embodiment, a polycation polymer is a branched polymer, a polymer that includes side chains of repeat units connecting onto the main chain of repeat units (which may be different from side chains already present in the monomers). In another embodiment, a polycation polymer is a crosslinked polymer, a polymer that includes interconnections between chains, either formed during polymerization (i.e., by choice of monomer) or after polymerizalion (i.e., by adding a specific reagent). In yet another embodiment, a polycation polymer is a network polymer, a crosslinked polymer that includes numerous interconnections between chains such that the entire polymer is, or could be, a single molecule.

Polycationic compositions may be substantially monodisperse or substantially polydisperse. A substantially monodisperse composition comprises polymer molecules, substantially all of which have the same chain length. A substantially polydisperse composition comprises polymer molecules with a variety of chain lengths (and hence molecular weights).

Polycations can have a wide range of molecular weights. The molecular weight of a polycation in a polycationic composition can vary depending on the particular polycationic compound (e.g., a polypeptide or a non-peptide), the rate of release of the polycation (e.g., from a gel), the degree of potency desired, etc. In some embodiments, a polycation can have a molecular weight greater than 1 kD, greater than 5 kD, greater than 10 kD, greater than 15 kD, greater than 20 kD, greater than 25 kD, greater than 30 kD, greater than 40 kD, greater than 50 kD, or greater than 60 kD, greater than 70 kD, greater than 80 kD, greater than 90 kD, greater than 100 kD, greater than 150 kD, greater than 200 kD, or greater. In other embodiments, a polycation can have a molecular weight between 1-5 kD, between 6-10 kD, between 11-15 kD, between 16-25 kD, or between 26-30 kD. However, other sizes may be used as the invention is not limited in this respect. Molecular weights can be determined by those of ordinary skill in the art by methods such as size-exclusion chromatography and/or multi-angle laser light scattering techniques.

The relative basicity of a polycation can vary. In some cases, a polycationic composition comprises a 'strong' polycation, which completely retains its charge in solution for most reasonable pH values. In other cases, a polycationic composition comprises a 'weak' polycation, i.e., whose charge can be substantially changed by proton transfer to or from the aqueous medium, in the pH range of ~2 to ~10. Polycations of different basicity can be used in polycationic compositions of the invention. A polycation may have a pKb value, for instance, between 2-10, between 2-4, between 5-7, between 8-10, between 2-5, or between 6-10.

Polycations can have varying degrees of solubility in a composition (e.g., varying degrees of water solubility) and/or when delivered to a target region. The solubility of a polycation can be changed, for example, by complexing the polycation with a polyanion, by solvent changes (e.g., by changing the ionic strength of the solvent), and by temperature changes. Polycations can be present in a polycationic composition as a solid (e.g., a precipitate), a gel, or a solution.

If desired, polycations can be combined with an appropriate amount of an agent in a polycationic composition. Agents may be pharmacologically active, meaning they may induce a desired systemic or local effect in addition to the effect of the polycation, or agents may be pharmacologically inactive. In one embodiment, the agent complexes with the polycation in the polycationic composition. In another embodiment, the agent may act as a carrier agent for the polycation or another component of the composition. In another embodiment, the agent may control the release of the polycation from the polycationic composition into the target region. In another embodiment, the agent can modulate (e.g., increase or decrease) the potency of the polycation or another component of the composition. In some cases, the agent may have one or more of the functions listed above, or, the agent may be added to the composition for different purposes.

In some cases, the agent is a polyanion. Any of a variety of polyanions may be used, non-limiting examples including glycosaminoglycans, such as chondroitin sulfate, heparin/heparan sulfate, keratin sulfate, dermatan sulfate, and hyaluronic acid, synthetic polypeptides such as polyglutamic acid and polyaspartic acid, and randomly-structured nucleic acids. In some instances, polar polymers such as polyethylene glycol, and/or neutral polymers such as polyvinylalcohol and polyvinylpyrrolidine, can be combined with polycations. Of course, the amount, molecular weight, degree of branching, etc. of the agent in the composition can vary.

According to certain embodiments of the invention, polycations can be complexed with agents such as polyanions. Polycations and polyanions can be weakly or strongly complexed. In some instances, the rate of delivery of a polycation to a targeted area, and/or the potency of a polycation, can be controlled by complexing the polycation with a suitable polyanion. For example, polylysine can be complexed with chondroitin sulfate (CS) and the toxicity of polylysine in a composition can be decreased by adding appropriate amounts of CS. In preferred embodiments, a polyanion is added in an amount sufficient to counterbalance some (e.g, 30%, 40%, 50%, 60%, 70%, 80%, 90%, etc.), but not all, of the positive charges on the polycation. It should be appreciated that the number of positive charges on a polycation and the number of negative charges on a polyanion can be determined and the amount of each molecule to be added can be calculated such that the resulting complex retains a net positive charge. For example, adding equal weights of polylysine and chondroitin sulfate results in a complex with a net positive charge (based on the molecular weights of lysine and chondroitin sulfate and based on a charge of +1 per lysine moiety and −2 per chondroitin sulfate moiety). In some embodiments, polylysine molecules of approximately 100 kD size are used. The size of the polycation that is used will determine, in part, the net charge per molecule of polycation that is retained after complexation with a predetermined amount of couterion.

In some cases, polycations and polyanions can be complexed into nanoparticles. In one embodiment, a polycation and a polyanion are complexed into micelles, whose sizes can be modified by changing the chain lengths of the polymer. In another embodiment, polycations and polyanions can form polyelectrolyte multilayers (PEMs). PEMs are multilayer complexes comprising alternating layers of polycations and polycations. One or more of the layers may be, or may include, a therapeutically active compound that can be delivered to a targeted area of a patient.

In one aspect of the invention, a polycationic composition comprises a polycation having a low net positive charge density. Polycations may comprise, for instance, a first set of repeat units that are neutral and a second set of repeat units that are positively charged. The average ratio of the number of neutral repeat units to the number of positively charged repeat units of the polycations in the composition may be less than 1:5, less than 1:2, less than 1:1, less than 2:1, less than 5:1, less than 10:1, less than 20:1, less than 30:1, less than 50:1, less than 70:1, less than 100:1, or less than 200:1. However, other ratios may be used as the invention is not limited in this respect. In some cases, the average overall charge of a polycation molecule in a composition of the invention may be less than +2000, less than +1000, less than +700, less than +500, less than +400, less than +300, less than +400, less than +300, less than +200, less than +100, or less than +50. However, higher or lower positive charges may be useful, depending partly on the size of the molecule.

In some embodiments, a polycation can comprise a first set of repeat units that are negatively charged and a second set of repeat units that are positively charged. A repeat unit of the negatively and/or positively charged units may optionally comprise multiple charges. For instance, each negatively charged repeat unit may contain two negative charges, while each positively charged repeat unit may contain one positive charge. Of course, other configurations are also possible. In some instances, all or portions of the negatively charged repeat units can be neutralized (i.e., complexed) with all or portions of the positively charged repeat units, so long as the overall charge of the polymer is positive. The average ratio of the number of positively charged repeat units to the number of negatively charged repeat units of the polycations in the composition may be less than 1:2, less than 1:1, less than 1.5:1, less than 2:1, less than 3:1, less than 4:1; less than 5:1, less than 10:1, less than 20:1, less than 30:1, or less than 50:1. In some embodiments, the average ratio of the number of positive charges to the number of negative charges of the polycations in the composition may be less than 1.5:1, less than 2:1, less than 3:1, less than 4:1; less than 5:1, less than 10:1, less than 20:1, less than 30:1, or less than 50:1. In some cases, the average overall charge of the polycations in the composition is less than 2000+, less than +1000, less than +700, less than +500, less than +400, less than +300, less than +400, less than +300, less than +200, less than +100, or less than +50. However, higher or lower positive charges may be useful, depending partly on the size of the molecule.

In certain embodiments, polycations can be complexed with anions or polyanions that are external to the polycation (i.e., the anion or polyanion is not attached to the backbone of the polycation). The polycation, in this instance, may be of the type having one or more types of positively charged repeat units, having both positively charged and negatively charged repeat units, or having both positively charged and neutral repeat units. The polyanion that complexes with the polycation may have, for instance, both negatively and positively charged repeat units, so long as the polyanion has an overall net negative charge. The average ratio of the number of positively charged repeat units to the number of negatively charged repeat units of the polycation-polyanion complex in a polycationic composition may be less than 1:2, less than 1:1, less than 1.5:1, less than 2:1, less than 3:1, less than 4:1; less than 5:1, less than 10:1, less than 20:1, less than 30:1, or less than 50:1. In some embodiments, the average ratio of the number of positive charges to the number of negative charges of the polycation-polyanion complex in a polycationic composition may be less than 1.5:1, less than 2:1, less than 3:1, less than 4:1; less than 5:1, less than 10:1, less than 20:1, less than 30:1, or less than 50:1. The average overall charge of a polycation-polyanion complex may be less than 2000+, less than +1000, less than +700, less than +500, less than +400, less than +300, less than +400, less than +300, less than +200, less than +100, or less than +50. However, higher or lower positive charges may be useful, depending partly on the size of the molecule.

In another embodiment, a polycationic composition comprises a polycation having a number of its positive charges neutralized while the polycation has an overall net positive charge. For instance, the average polycation of the composition may have 10-15%, 15-20%, 20-25%, 25-30%, 30-40%, 40-50%, 50-55%, 55-60%, 60-65%, 65-70%, 70-75%, 75-80%, 80-85%, 85-90%, 90-95%, or 95-99% of its positive charges neutralized.

In aspects of the invention, polycationic compositions can be provided in a number of different forms for administration. For instance, a polycationic composition may be in the form of a solid, solution, suspension, foam, or a gel.

In certain aspects, a polycationic composition may be provided in a form that can be localized when administered to a subject (e.g., substantially restricted to a region of administration in the body of the subject). However, it should be appreciated that in some embodiments a polycationic composition of the invention may be provided and administered as a solution or solid (e.g., powder) without any carrier compound or matrix material (e.g., without a gel or cream etc.).

Accordingly, aspects of the invention involve methods and compositions for localizing polycations within certain regions of the body. In some instances, localization can prevent leakage of harmful amounts of polycations into the circulation where the polycation may be toxic. Localization may also limit the effects of polycations (e.g., sclerosis and fibrosis) to the specific site of administration. In one particular aspect, localization can be achieved by administering a polycationic composition comprising a gel. In another aspect, localization can be achieved by combining a polycation with a second species, such as a polyanion.

In certain embodiments, biodisintegrable polyelectrolytes (polycations and polyanions) can be used. As used herein, a "biodisintegrable material" is a material that undergoes dissolution, degradation, absorption, erosion, corrosion, resorption and/or other disintegration processes in a patient.

SELECTED HYDROGEL COMPOSITIONS OF THE INVENTION. One aspect of the invention relates to a hydrogel comprising a polymer comprising a plurality of pendent hydroxyl groups, a crosslinker, and a sclerosing agent.

In certain embodiments, the present invention relates to the aforementioned hydrogel, further comprising a gas, thereby forming a foamed hydrogel.

In certain embodiments, the present invention relates to the aforementioned hydrogel, wherein said gas is oxygen.

In certain embodiments, the present invention relates to the aforementioned hydrogel, wherein said hydrogel is in contact with a mammalian tissue.

In certain embodiments, the present invention relates to the aforementioned hydrogel, wherein said hydrogel is in contact with a mammalian pulmonary tissue.

In certain embodiments, the present invention relates to the aforementioned hydrogel, wherein said hydrogel contacts an interior surface of a mammalian pulmonary tissue.

In certain embodiments, the present invention relates to the aforementioned hydrogel, wherein said hydrogel contacts an interior surface of a mammalian alveoli.

In certain embodiments, the present invention relates to the aforementioned hydrogel, wherein said hydrogel contacts an interior surface of a mammalian alveoli and partially or completely fills the mammalian alveoli.

In certain embodiments, the present invention relates to the aforementioned hydrogel, wherein said hydrogel comprises greater than about 80% water (w/w).

In certain embodiments, the present invention relates to the aforementioned hydrogel, wherein said hydrogel comprises greater than about 90% water (w/w).

In certain embodiments, the present invention relates to the aforementioned hydrogel, wherein said hydrogel comprises greater than about 95% water (w/w).

In certain embodiments, the present invention relates to the aforementioned hydrogel, wherein upon combination of said polymer, said crosslinker and said sclerosing agent, said hydrogel is formed in about 30 seconds.

In certain embodiments, the present invention relates to the aforementioned hydrogel, wherein upon combination of said polymer, said crosslinker and said sclerosing agent, said hydrogel is formed in about 1 minute.

In certain embodiments, the present invention relates to the aforementioned hydrogel, wherein upon combination of said polymer, said crosslinker and said sclerosing agent, said hydrogel is formed in about 2 minutes.

In certain embodiments, the present invention relates to the aforementioned hydrogel, wherein upon combination of said polymer, said crosslinker and said sclerosing agent, said hydrogel is formed in about 5 minutes.

In certain embodiments, the present invention relates to the aforementioned hydrogel, wherein upon combination of said polymer, said crosslinker and said sclerosing agent, said hydrogel is formed in about 15 minutes.

In certain embodiments, the present invention relates to the aforementioned hydrogel, wherein upon combination of said polymer, said crosslinker and said sclerosing agent, said hydrogel is formed in about 30 minutes.

In certain embodiments, the present invention relates to the aforementioned hydrogel, wherein said hydrogel degrades under physiological conditions in about 1 to about 12 weeks.

In certain embodiments, the present invention relates to the aforementioned hydrogel, wherein said hydrogel degrades under physiological conditions in about 1 to about 6 weeks.

In certain embodiments, the present invention relates to the aforementioned hydrogel, wherein said hydrogel degrades under physiological conditions in about 1 to about 4 weeks.

In certain embodiments, the present invention relates to the aforementioned hydrogel, wherein said hydrogel degrades under physiological conditions in about 2 to about 5 weeks.

In certain embodiments, the present invention relates to the aforementioned hydrogel, wherein said polymer comprises a plurality of 1,2-diols.

In certain embodiments, the present invention relates to the aforementioned hydrogel, wherein said 1,2-diols are cis-1,2-diols and are part of five-membered or six-membered rings.

In certain embodiments, the present invention relates to the aforementioned hydrogel, wherein said 1,2-diols are a cis-1,2-diols and are part of six-membered rings.

In certain embodiments, the present invention relates to the aforementioned hydrogel, wherein said 1,2-diols are linear 1,2-diols.

In certain embodiments, the present invention relates to the aforementioned hydrogel, wherein said polymer comprises a plurality of 1,3-diols.

In certain embodiments, the present invention relates to the aforementioned hydrogel, wherein said 1,3-diols are a cis-1,3-diols and are part of five-membered or six-membered rings.

In certain embodiments, the present invention relates to the aforementioned hydrogel, wherein said 1,3-diols are cis-1,3-diols and are part of six-membered rings.

In certain embodiments, the present invention relates to the aforementioned hydrogel, wherein said 1,3-diols are linear 1,3-diols.

In certain embodiments, the present invention relates to the aforementioned hydrogel, wherein said polymer is a polysaccharide comprising a cis-1,2-diol.

In certain embodiments, the present invention relates to the aforementioned hydrogel, wherein said polymer is guar gum, xanthan gum, an α-glucan, a galactomannan, or a glucomannan.

In certain embodiments, the present invention relates to the aforementioned hydrogel, wherein said polymer is selected from the group consisting of polyhydroxyethylmethacrylates, polyvinyl alcohols, polyacrylamides, poly-N-vinylpyrolidones, polyacrylic acids, polymethacrylic acids, polyethylene amines, and salts, esters, and copolymers thereof.

In certain embodiments, the present invention relates to the aforementioned hydrogel, wherein said polymer is polyvinyl alcohol.

In certain embodiments, the present invention relates to the aforementioned hydrogel, wherein said polyvinyl alcohol has a hydrolysis grade of greater than about 70.

In certain embodiments, the present invention relates to the aforementioned hydrogel, wherein said polyvinyl alcohol has a hydrolysis grade of greater than about 85.

In certain embodiments, the present invention relates to the aforementioned hydrogel, wherein said polyvinyl alcohol has a weight average molecular weight of between about 25,000 g/mol and about 250,000 g/mol.

In certain embodiments, the present invention relates to the aforementioned hydrogel, wherein said polyvinyl alcohol has a weight average molecular weight of between about 50,000 g/mol and about 150,000 g/mol.

In certain embodiments, the present invention relates to the aforementioned hydrogel, wherein said polyvinyl alcohol has a weight average molecular weight of about 100,000 g/mol.

In certain embodiments, the present invention relates to the aforementioned hydrogel, wherein said polymer is copolymer of a first monomer and a second monomer; wherein said first monomer is a polyvinyl alcohol-yielding monomer; and said second monomer is selected from the group consisting of olefins, propylene, 1-butene, isobutene, acrylic acid, acrylic acid salts, acrylates, methyl acrylate, ethyl acrylate, n-propyl acrylate, i-propyl acrylate, n-butyl acrylate, i-butyl acrylate, t-butyl acrylate, 2-ethylhexyl acrylate, dodecyl acrylate, octadecyl acrylate, methacrylic acid, methacrylic acid salts, methacrylates, methyl methacrylate, ethyl methacrylate, n-propyl methacrylate, i-propyl methacrylate, n-butyl methacrylate, i-butyl methacrylate, t-butyl methacrylate, 2-ethylhexyl methacrylate, dodecyl methacrylate, octadecyl methacrylate, acrylamide, N-methylacrylamide, N-ethylacrylamide, N,N-dimethylacrylamide, diacetonacrylamide, acrylamidopropanesulfonic acid, salts of acrylamidopropanesulfonic acid, acrylamidopropyldimethylamine, salts of acrylamidopropyldimethylamine, N-methylolacrylamide, methacrylamide, N-methylmethacrylamide, N-ethylmethacrylamide, methacrylamidopropanesulfonic acid, salts of methacrylamidopropanesulfonic acid, methacrylamidopropyldimethylamine, salts of methacrylamidopropyldimethylamine, N-methylolmethacrylamide, N-vinylamides, N-vinylformamide, N-vinylacetamide, N-vinylpyrrolidone, vinyl ethers, methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether, nitriles, acrylonitrile, methacrylonitrile, vinyl halides, vinyl chloride, vinylidene chloride, vinyl fluoride, vinylidene fluoride, allyl compounds, allyl acetate, allyl chloride, maleic acid, salts of maleic acid, maleic acid esters, itaconic acid, salts of itaconic acid, itaconic acid esters, vinylsilyl compounds, vinyltrimethoxysilane, isopropenyl acetate, N-vinylamides, N-vinylformamide, N-vinylacetamide, and N-vinylpyrrolidone.

In certain embodiments, the present invention relates to the aforementioned hydrogel, wherein said copolymer is a block copolymer, random copolymer, graft polymer, or branched copolymer.

In certain embodiments, the present invention relates to the aforementioned hydrogel, wherein said copolymer comprises about 50 mol % of the first monomer.

In certain embodiments, the present invention relates to the aforementioned hydrogel, wherein said copolymer comprises about 60 mol % of the first monomer.

In certain embodiments, the present invention relates to the aforementioned hydrogel, wherein said copolymer comprises about 70 mol % of the first monomer.

In certain embodiments, the present invention relates to the aforementioned hydrogel, wherein said copolymer comprises about 80 mol % of the first monomer.

In certain embodiments, the present invention relates to the aforementioned hydrogel, wherein said copolymer comprises about 90 mol % of the first monomer.

In certain embodiments, the present invention relates to the aforementioned hydrogel, wherein said copolymer comprises about 95 mol % of the first monomer.

In certain embodiments, the present invention relates to the aforementioned hydrogel, wherein said crosslinker is water soluble at a concentration of at least about 1 mg/mL.

In certain embodiments, the present invention relates to the aforementioned hydrogel, wherein said crosslinker is water soluble at a concentration of at least about 2.5 mg/mL.

In certain embodiments, the present invention relates to the aforementioned hydrogel, wherein said crosslinker is water soluble at a concentration of at least about 5 mg/mL.

In certain embodiments, the present invention relates to the aforementioned hydrogel, wherein said crosslinker is water soluble at a concentration of at least about 10 mg/mL.

In certain embodiments, the present invention relates to the aforementioned hydrogel, wherein said crosslinker is water soluble at a concentration of at least about 20 mg/mL.

In certain embodiments, the present invention relates to the aforementioned hydrogel, wherein said crosslinker is derived from a compound selected from the group consisting of boric acid, borates, boronic acids, boronates and boroxines.

In certain embodiments, the present invention relates to the aforementioned hydrogel, wherein said crosslinker is derived from boric acid or a borate.

In certain embodiments, the present invention relates to the aforementioned hydrogel, wherein said crosslinker is derived from boric acid, sodium borate or potassium borate.

In certain embodiments, the present invention relates to the aforementioned hydrogel, wherein said crosslinker is derived from a boronic acid, a boronate, or a boroxine.

In certain embodiments, the present invention relates to the aforementioned hydrogel, wherein said crosslinker is derived from compounds selected from the group consisting of alkyl boronic acids, alkyl boronates, alkyl boroxine, alkenyl boronic acids, alkenyl boronates, alkenyl boroxine, aryl boronic acids, aryl boronates, aryl boroxine, heteroaryl boronic acids, heteroaryl boronates, heteroaryl boroxine, aralkyl boronic acid, aralkyl boronates, aralkyl boroxine, heteroaralkyl boronic acids, heteroaralkyl boronates and heteroaralkyl boroxine.

In certain embodiments, the present invention relates to the aforementioned hydrogel, wherein said crosslinker is derived from an optionally-substituted phenyl boronic acid, an optionally-substituted phenyl boronate, or an optionally-substituted phenyl boroxine.

In certain embodiments, the present invention relates to the aforementioned hydrogel, wherein said crosslinker is derived from compounds selected from the group consisting of trans-2-phenylvinylboronic acid, trans-2-(4-chlorophenyl)vinylboronic acid, trans-2-(4-fluorophenyl)vinylboronic acid, trans-2-(4-methoxyphenyl)vinylboronic acid, trans-2-(4-(trifluoromethyl)phenyl)vinylboronic acid, trans-1-hexen-1-ylboronic acid, trans-1-octen-1-ylboronic acid, trans-2-[3-(trifluoromethyl)phenyl]vinylboronic acid, trans-2-(4-biphenyl)vinylboronic acid, trans-2-(3-methoxyphenyl)vinylboronic acid, trans-2-chloromethylvinylboronic acid, ($\epsilon$)-5-chloro-1-penteneboronic acid, trans-2-(4-methylphenyl)vinylboronic acid, $\alpha$-phenyl vinylboronic acid, cis-propenylboronic acid, trans-propenylboronic acid, 1-pentenylboronic acid, 2-cyclohexylvinylboronic acid, 1-benzothiophen-2-ylboronic acid, n-boc-2-pyrryl-boronic acid, 2-thienylboronic acid, thiophene-3-boronic acid, 2-furanboronic acid, 2,5-thiophenediboronic acid, 2-formyl-3-thiopheneboronic acid, 3-formyl-2-thiopheneboronic acid, 5-acetyl-2-thiopheneboronic acid, 5-chloro-2-thienylboronic acid, benzofuran-2-ylboronic acid, 4-dibenzofuranboronic acid, benzothiophen-2-ylboronic acid, 4-dibenzothipheneboronic acid, thianaphthene-3-boronic acid, 3-pyridineboronic acid, 3-furanboronic acid, 5-methyl-2-thiopheneboronic acid, thianthrene-1-boronic acid, 5-methyl-2-furanboronic acid, 5-formyl-2-furanboronic acid, 5-formyl-2-thiopheneboronic acid, 4-methyl-3-thiopheneboronic acid, 5-bromothiophene-2-boronic acid, N-Boc-indole-2-boronic acid, 1-(phenylsulfonyl)-2-indoleboronic acid, 1-(phenylsulfonyl)-3-indoleboronic acid, 4-pyridineboronic acid, 2-chloro-5- pyrideboronic acid, 3-aminophenylboronic acid monohydrate, 3-nitrophenylboronic acid, o-tolylboronic acid, m-tolylboronic acid, p-tolylboronic acid, 3-aminophenylboronic acid hydrochloride, π-phenylenediboronic acid, 3-chlorophenylboronic acid, 4-chlorophenylboronic acid, 4-fluorophenylboronic acid, 4-vinylphenylboronic acid, 4-methoxyphenylboronic acid, 2-formylphenylboronic acid, 4-formylphenylboronic acid, 3-(trifluoromethyl)phenylboronic acid, 4-(trifluoromethyl)phenylboronic acid, 3-bromophenylboronic acid, 3-ethoxyphenylboronic acid, 3-fluorophenylboronic acid, 3-formylphenylboronic acid, 3-iodophenylboronic acid, 3-methoxyphenylboronic acid, 2-(trifluoromethyl)phenylboronic acid, 3,5-dichlorophenylboronic acid, 2-chlorophenylboronic acid, 2-fluorophenylboronic acid, 2-methoxyphenylboronic acid, 2-ethoxyphenylboronic acid, 4-ethoxyphenylboronic acid, 3-carboxyphenylboronic acid, 4-carboxyphenylboronic acid, 4,4'-biphenyldiboronic acid, 4-(methylthio)phenylboronic acid, 2,4-difluorophenylboronic acid, 3,4-difluorophenylboronic acid, pentafluorophenylboronic acid, 2,6-difluorophenylboronic acid, 2-acetylphenylboronic acid, 3-acetylphenylboronic acid, 4-acetylphenylboronic acid, 3,5-bis(trifluoromethyl)phenylboronic acid, 3,4-dichlorophenylboronic acid, 3,5-difluorophenylboronic acid, 4-iodophenylboronic acid, 2-bromophenylboronic acid, 4-tert-butylphenylboronic acid, 2,6-dimethylphenylboronic acid, 3,5-dimethylphenylboronic acid, 2,6-dimethoxyphenylboronic acid, 3,4-dimethoxyphenylboronic acid, naphthalene-2-boronic acid, 2-naphthylboronic acid, 4-phenoxyphenylboronic acid, 4-biphenylboronic acid, 2,4-dimethoxyphenylboronic acid, 2,5-dimethoxyphenylboronic acid, 2,3-dimethylphenylboronic acid, 2,5-dimethylphenylboronic acid, 4-(dimethylamino)phenylboronic acid, 5-fluoro-2-methoxyphenylboronic acid, 4-fluoro-3-methylphenylboronic acid, 3,5-dibromophenylboronic acid, 4-ethylphenylboronic acid, 3,4-(methylenedioxy)phenylboronic acid, 3-(trifluoromethoxy)phenylboronic acid, 4-(trifluoromethoxy)phenylboronic acid, 2-fluoro-4-biphenylylboronic acid, 3-chloro-4-fluorophenylboronic acid, 5-chloro-2-methoxyphenylboronic acid, 5-formyl-2-methoxyphenylboronic acid, 2,3,4-trimethoxyphenylboronic acid, 2,5-dichlorophenylboronic acid, 4-(hydroxymethyl)phenylboronic acid, 4-borono-dl-phenylalanine, 5-bromo-2-methoxyphenylboronic acid, 2-chloro-6-methoxyphenylboronic acid, 2-fluoro-6-methoxyphenylboronic acid, 5-bromo-2-ethoxyphenylboronic acid, 3-(hydroxymethyl)phenylboronic acid, 3-formyl-4-methoxyphenylboronic acid, 3-cyanophenylboronic acid, 2,5-difluorophenylboronic acid, 2,3-difluorophenylboronic acid, 2,3-dichlorophenylboronic acid, 2-(methylthio)phenylboronic acid, 2-benzyloxyphenylboronic acid, 2,4-dichlorophenylboronic acid, 2-cyanophenylboronic acid, 4-cyanophenylboronic acid, 4-methyl-1-naphthaleneboronic acid, 4-methyl-3-nitrophenylboronic acid, 2-phenoxyphenylboronic acid, 4-butylphenylboronic acid, 4-propylphenylboronic acid, 2-ethylphenylboronic acid, 2-ethoxy-1-naphthaleneboronic acid, 6-methoxy-2-naphthaleneboronic acid, 6-ethoxy-2-naphthaleneboronic acid, 3-(trimethylsilyl)phenylboronic acid, 4-(trimethylsilyl)phenylboronic acid, 3-hydroxyphenylboronic acid, 4-hydroxyphenylboronic acid, 3-mercaptophenylboronic acid, 4-mercaptophenylboronic acid, 3-(tert-butyldimethylsilyoxy)phenylboronic acid, 2,3,4-trifluorophenylboronic acid, 2,3,6-trifluorophenylboronic acid, 2,4,6-trifluorophenylboronic acid, 2,4,5-trifluorophenylboronic acid, 2,3,5-trifluorophenylboronic acid, 3,4,5-trifluorophenylboronic acid, 4-benzoylphenylboronic acid, 3-benzyloxyphenylboronic acid, 3-biphenylboronic acid, 2-biphenylboronic acid, 3-fluoro-4-formylphenylboronic acid, 2,4,6-trimethylphenylboronic acid, 2,4,5-trimethylphenylboronic acid, 3-isopropoxyphenylboronic acid, 2-isopropoxyphenylboronic acid, 4-isopropoxyphenylboronic acid, 2-butoxyphenylboronic acid, 3-butoxyphenylboronic acid, 4-butoxyphenylboronic acid, 3-bromo-2-ethoxy-5-fluorophenylboronic acid, 5-chloro-2-ethoxyphenylboronic acid, 1-pyreneboronic acid, 4-bromo-2,6-difluorophenylboronic acid, 3-chloro-2-fluorophenylboronic acid, 5-chloro-2-fluorophenylboronic acid, 3-bromo-2,6-difluorophenylboronic acid, 2-chloro-6-fluoro-3-methylphenylboronic acid, 2-chloro-6-fluoro-5-methylphenylboronic acid, 5-chloro-2-fluoro-3-methylphenylboronic acid, 4-propoxyphenylboronic acid, 3-propoxyphenylboronic acid, 2-propoxyphenylboronic acid, 2,3-dimethoxyphenylboronic acid, 2-fluoro-5-(trifluoromethyl)phenylboronic acid, 3-bromo-2-fluorophenylboronic acid, 3-fluoro-4-methoxyphenylboronic acid, 4-ethoxy-3-fluorophenylboronic acid, 3-fluoro-4-isopropoxyphenylboronic acid, 4-butoxy-3-chlorophenylboronic acid, 3-chloro-4-isopropoxyphenylboronic acid, 3-chloro-4-propoxyphenylboronic acid, 3-chloro-4-ethoxyphenylboronic acid, 3-chloro-4-methoxyphenylboronic acid, 2-butoxy-5-fluorophenylboronic acid, 5-fluoro-2-isopropoxyphenylboronic acid, 5-methyl-2-propoxyphenylboronic acid, 4-fluoro-2-methylphenylboronic acid, 2-isopropoxy-5-methylphenylboronic acid, 2-butoxy-5-methylphenylboronic acid, 5-fluoro-2-propoxyphenylboronic acid, 4-acetamidophenylboronic acid, 4-(n-boc-amino)phenylboronic acid, 3-acetamidophenylboronic acid, 2-chloro-6-fluorophenylboronic acid, 9,9-dihexylfluorene-2,7-dioronic acid, 2-fluoro-4-methylphenylboronic acid, 3-fluoro-4-methylphenylboronic acid, 2-fluoro-5-methylphenylboronic acid, acenaphthene-5-boronic acid, 3,5-diformylphenylboronic acid, 2-ethoxy-5-methylphenylboronic acid, 2-methoxy-5-methylphenylboronic acid, 9,9-dioctylfluorene-2,7-diboronic acid, 2,3-difluoro-4-formylphenylboronic acid, 9,9-didodecylfluorene-2,7-diboronic acid, 9,9-di(2'-ethylhexyl)fluorene-2,7-diboronic acid, 4-ethoxycarbonylphenylboronic acid, 3-ethoxycarbonylphenylboronic acid, n-(4-phenylboronic)succinamic acid, 3-methoxycarbonylphenylboronic acid, 3-bromo-2-butoxyphenylboronic acid, 2,6-difluoro-4-methoxyphenylboronic acid, 2-fluoro-5-iodophenylboronic acid, 2-fluoro-3-iodophenylboronic acid, 5-bromo-2-fluorophenylboronic acid, 2-bromo-6-fluorophenylboronic acid, 4-bromo-2,3,5,6-tetrafluorophenylboronic acid, 2-fluoro-3-methoxyphenylboronic acid, 2-fluoro-3-methoxyphenylboronic acid, 2-fluoro-5-propoxyphenylboronic acid, 5-ethoxy-2-fluorophenylboronic acid, 2-ethoxy-6-fluorophenylboronic acid, 4-methoxycarbonylpheynlboronic acid, 4-butoxy-2-methylphenylboronic acid, 4-ethoxy-2-methylphenylboronic acid, 2-ethoxy-5-fluorophenylboronic acid, 4-methoxy-3-methylphenylboronic acid, 4-benzyloxy-3-chlorophenylboronic acid, 3-bromo-5-methyl-2-methoxyphenylboronic acid, 3-bromo-2-ethoxy-5-methylphenylboronic acid, 3-bromo-2-isopropoxy-5-methylphenylboronic acid, 3-bromo-5-methyl-2-propoxyphenylboronic acid, 3-bromo-2-butoxy-5-methylphenylboronic acid, 3-bromo-2-propoxyphenylboronic acid, 2-fluoro-5-methoxyphenylboronic acid, 3-bromo-2-isopropoxyphenylboronic acid, 3-(ethylthio)phenylboronic acid, 2,4-difluoro-3-formylphenylboronic acid, 4-butoxy-3, 5-dimethylphenylboronic acid, 3,5-dimethyl-4-propoxyphenylboronic acid, 3,5-dimethyl-4-ethoxyphenylboronic acid, 3,5-dimethyl-4-methoxyphenylboronic acid, 3-benzyloxy-2,6-difluorophenylboronic acid, 3-(2'-chlorobenzyloxy)phenylboronic acid, 4-(3',5'-dimethoxybenzyloxy)phenylboronic acid, 3-(3',5'-dimethoxybenzyloxy)phenylboronic acid, 2-bromo-5,6-difluorophenylboronic acid, 2-fluoro-6-propoxyphenylboronic acid, 2-benzyloxy-3-bromo-5-methylphenylboronic acid, 2-(2'-chlorobenzyloxy)phenylboronic acid, 3-aminophenylboronic acid, 4-bromophenylboronic acid, 1-naphthylboronic acid, phenylboronic acid, butylboronic acid, methylboronic acid, (2-methylpropyl)boronic acid, and the corresponding boronates and boroxines thereof.

In certain embodiments, the present invention relates to the aforementioned hydrogel, wherein said crosslinker is derived from a bis-boronic acid or a bis-boronate.

In certain embodiments, the present invention relates to the aforementioned hydrogel, wherein said sclerosing agent is water soluble at a concentration of at least about 1 mg/mL.

In certain embodiments, the present invention relates to the aforementioned hydrogel, wherein said sclerosing agent is water soluble at a concentration of at least about 2.5 mg/mL.

In certain embodiments, the present invention relates to the aforementioned hydrogel, wherein said sclerosing agent is water soluble at a concentration of at least about 5 mg/mL.

In certain embodiments, the present invention relates to the aforementioned hydrogel, wherein said sclerosing agent is water soluble at a concentration of at least about 10 mg/mL.

In certain embodiments, the present invention relates to the aforementioned hydrogel, wherein said sclerosing agent is water soluble at a concentration of at least about 20 mg/mL.

In certain embodiments, the present invention relates to the aforementioned hydrogel, wherein said sclerosing agent comprises a polycation.

In certain embodiments, the present invention relates to the aforementioned hydrogel, wherein said polycation is a polyamine, a polysaccharide, or a polyamino acid.

In certain embodiments, the present invention relates to the aforementioned hydrogel, wherein said polycation is a polysaccharide or a polyamino acid.

As herein described it may sometimes also be useful to use cationic polymers containing a mixture of different types of amino groups, some predominantly charged at neutral pH (e.g., poly(L)lysine) and others subject to significant protonation by the falling pH during endosomal acidification (e.g., L-histidine). In some other embodiments non-polypeptide synthetic polymers may be used, including synthetic polymers containing a primary or tertiary amino group or a quaternary ammonium group.

In certain embodiments, the present invention relates to the aforementioned hydrogel, wherein said polycation is polylysine, polyarginine, polyomithine, chitosan polycations, gelatin polycations, or albumin polycations.

In certain embodiments, the present invention relates to the aforementioned hydrogel, wherein said polycation is a poly(amino acid), wherein said poly(amino acid) comprises a plurality of amino acids independently selected from the group consisting of Lys and Arg; and a plurality of amino acids independently selected from the group consisting of Gly, Ala, Val, Leu, Ile, Met, Pro, Phe, Trp, Asn, Gln, Ser, Thr, Tyr, Cys, and His; provided that no less than twenty-five percent of the amino acids is independently selected from the group consisting of Lys and Arg; further provided that no more than five percent of the amino acids is independently selected from the group consisting of Asp and Glu.

In certain embodiments, the present invention relates to the aforementioned hydrogel, wherein said polycation is a poly(amino acid), wherein said poly(amino acid) is represented by poly(X-Y), poly(X-Y-Y), or poly(X-Y-Y-Y), wherein X is independently for each occurrence Lys or Arg; and Y is independently for each occurrence Gly, Ala, Val, Leu, Ile, Met, Pro, Phe, Trp, Asn, Gln, Ser, Thr, Tyr, Cys, or His.

In certain embodiments, the present invention relates to the aforementioned hydrogel, wherein said polycation is a poly(amino acid), wherein said polycation is poly-L-lysine.

In certain embodiments, the present invention relates to the aforementioned hydrogel, wherein said polycation degrades under physiological conditions in about 1 to about 12 weeks.

In certain embodiments, the present invention relates to the aforementioned hydrogel, wherein said polycation degrades under physiological conditions in about 1 to about 6 weeks.

In certain embodiments, the present invention relates to the aforementioned hydrogel, wherein said polycation degrades under physiological conditions in about 1 to about 4 weeks.

In certain embodiments, the present invention relates to the aforementioned hydrogel, wherein said polycation degrades under physiological conditions in about 2 to about 5 weeks.

In certain embodiments, the present invention relates to the aforementioned hydrogel, further comprising a polyanion.

In certain embodiments, the present invention relates to the aforementioned hydrogel, wherein said polyanion is a polysaccharide or a polyamino acid.

In certain embodiments, the present invention relates to the aforementioned hydrogel, wherein said polyanion is selected from the group consisting of sodium alginate gelatin polyanions, hyaluronic acid, carrageenan, chondroitin sulfate, carboxymethylcellulose, polyglutamic acid, and polyaspartic acid.

In certain embodiments, the present invention relates to the aforementioned hydrogel, wherein said polyanion is chondroitin sulfate.

In certain embodiments, the present invention relates to the aforementioned hydrogel, wherein said polyanion degrades under physiological conditions in about 1 to about 12 weeks.

In certain embodiments, the present invention relates to the aforementioned hydrogel, wherein said polyanion degrades under physiological conditions in about 1 to about 6 weeks.

In certain embodiments, the present invention relates to the aforementioned hydrogel, wherein said polyanion degrades under physiological conditions in about 1 to about 4 weeks.

In certain embodiments, the present invention relates to the aforementioned hydrogel, wherein said polyanion degrades under physiological conditions in about 2 to about 5 weeks.

In certain embodiments, the present invention relates to the aforementioned hydrogel, wherein the ratio of the product of the mass of the polycation and the charge per mass ratio of the polycation to the product of the mass of the polyanion and the charge per mass ratio of the polyanion is greater than about 1.

In certain embodiments, the present invention relates to the aforementioned hydrogel, wherein the ratio of the product of the mass of the polycation and the charge per mass ratio of the polycation to the product of the mass of the polyanion and the charge per mass ratio of the polyanion is greater than about 1 and less than about 20.

In certain embodiments, the present invention relates to the aforementioned hydrogel, wherein the ratio of the product of the mass of the polycation and the charge per mass ratio of the polycation to the product of the mass of the polyanion and the charge per mass ratio of the polyanion is greater than about 5 and less than about 10.

In certain embodiments, the present invention relates to the aforementioned hydrogel, wherein the polycation and the polyanion form a precipitated complex.

In certain embodiments, the present invention relates to the aforementioned hydrogel, wherein said sclerosing agent is a peroxide.

In certain embodiments, the present invention relates to the aforementioned hydrogel, wherein said peroxide is hydrogen peroxide, a peroxyborate, a peroxyboric acid, a peroxycarbonate, a peroxycarbonic acid, an alkyl hydroperoxide, an aryl hydroperoxide, an aralkyl hydroperoxide, a peroxyacetate, or a peroxyacetic acid.

In certain embodiments, the present invention relates to the aforementioned hydrogel, wherein said peroxide is sodium perborate, sodium percarbonate, or sodium peracetate.

In certain embodiments, the present invention relates to the aforementioned hydrogel, further comprising an anti-infective.

In certain embodiments, the present invention relates to the aforementioned hydrogel, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifingal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned hydrogel, wherein said anti-infective is tetracycline.

In certain embodiments, the present invention relates to the aforementioned hydrogel, further comprising a contrast-enhancing agent.

In certain embodiments, the present invention relates to the aforementioned hydrogel, wherein said contrast-enhancing agent is selected from the group consisting of radiopaque materials, paramagnetic materials, heavy atoms, transition metals, lanthanides, actinides, dyes, and radionuclide-containing materials.

SELECTED METHODS OF THE INVENTION. Aspects of the invention relate to certain formulations of compositions that are useful for non-surgical lung volume reduction. According to the invention, lung volume reduction, a procedure that reduces lung size by removing damaged (e.g., over-expanded) regions of the lung, can be accomplished non-surgically by procedures carried out through the patient's trachea (e.g., by inserting devices and substances through a bronchoscope), rather than by procedures that disrupt the integrity of the chest wall (Ingenito et al., *Am. J. Resp. Crit. Care Med.* 164:295-301, 2001; Ingenito et al., *Am. J. Resp. Crit. Care Med.* 161:A750, 2000; Ingenito et al., *Am. J. Resp. Crit. Care Med.* 163:A957, 2001). In one aspect of the invention, non-surgical lung volume reduction is performed by introducing a material (e.g., a synthetic or biological material) into a target region of the lung to promote collapse of the target region. In one embodiment, the material promotes stable collapse by adhering to the collapsed tissue together (e.g., the material forms a hydrogel that adheres to the collapsed tissue) and/or by promoting scarring of the collapsed tissue.

According to the invention, where the lung is targeted, a target region of the lung may be collapsed by administering a substance that increases the surface tension of fluids lining the alveoli in the targeted region, the surface tension being increased to the point where the region of the lung collapses. The concentration of the active agents in the hydrogel compositions of the invention are described further below, but it is noted here that the concentrations will be sufficient to cause collapse of the targeted region. In one embodiment, the concentrations are sufficient to cause hydrogel formation and adhesion of the collapsed lung region. The hydrogel compositions described herein can be used not only for lung volume reduction and other tissue treatments, but also for use as medicaments, or for use in the preparation of medicaments, for treating patients who have a disease or condition that would benefit from lung volume reduction or one that can be treated with an implanted device (e.g., a stent or a valve, pump, or prosthetic device).

Once a patient is determined to be a candidate for BLVR, the target region of the lung can be identified using radiological studies (e.g., chest X-rays) and computed tomography scans. When the LVR procedure is subsequently performed, the patient is anesthetized and intubated, and can be placed on an absorbable gas (e.g., at least 90% oxygen and up to 100% oxygen) for a specified period of time (e.g., approximately 30 minutes). The region(s) of the lung that were first identified radiologically are then identified bronchoscopically.

Suitable bronchoscopes include those manufactured by Pentax, Olympus, and Fujinon, which allow for visualization of an illuminated field. The physician guides the bronchoscope into the trachea and through the bronchial tree so that the open tip of the bronchoscope is positioned at the entrance to target region (i.e., to the region of the lung that will be reduced in volume). The bronchoscope can be guided through progressively narrower branches of the bronchial tree to reach various subsegments of either lung. For example, the bronchoscope can be guided to a subsegment within the upper lobe of the patient's left lung.

The balloon catheter may then be guided through the bronchoscope to a target region of the lung. When the catheter is positioned within the bronchoscope, the balloon is inflated so that material passed through the catheter will be contained in regions of the lung distal to the balloon. This is particularly useful in the methods of the present invention, which include the introduction of liquids into the selected region of the lung.

One aspect of the invention relates to a method for reducing lung volume in a patient comprising the steps of: advancing into a region of a patient's lung via said patient's trachea a multi-lumen catheter lumen through a bronchoscope; and co-administering, through the multi-lumen catheter, a first mixture comprising a first amount of a polymer containing a plurality of pendent hydroxyl groups; a second mixture comprising a second amount of a crosslinker; a third mixture comprising a third amount of a sclerosing agent and optionally a fourth amount of a polyanion; thereby forming a hydrogel in said region.

In certain embodiments, the present invention relates to the aforementioned method, further comprising co-administering a gas, thereby forming a foamed hydrogel.

In certain embodiments, the present invention relates to the aforementioned method, wherein said gas is oxygen.

In certain embodiments, the present invention relates to the aforementioned method, wherein said method results in the deflation and atelactasis of said region of the lung.

In certain embodiments, the present invention relates to the aforementioned method, wherein said region of the lung has little or no physiological function.

In certain embodiments, the present invention relates to the aforementioned method, further comprising the step of inflating the region of the lung with a gas prior to formation of the hydrogel.

In certain embodiments, the present invention relates to the aforementioned method, wherein said gas is oxygen.

In certain embodiments, the present invention relates to the aforementioned method, wherein said multi-lumen catheter is a dual-catheter lumen.

In certain embodiments, the present invention relates to the aforementioned method, wherein the total amount of the first mixture, second mixture and third mixture is between about 5 mL and about 300 mL.

In certain embodiments, the present invention relates to the aforementioned method, wherein the total amount of the first mixture, second mixture and third mixture is between about 10 mL and about 100 mL.

In certain embodiments, the present invention relates to the aforementioned method, wherein the total amount of the first mixture, second mixture and third mixture is between about 10 mL and about 50 mL.

In certain embodiments, the present invention relates to the aforementioned method, wherein said patient is a human.

In certain embodiments, the present invention relates to the aforementioned method, wherein said patient has emphysema.

In certain embodiments, the present invention relates to the aforementioned method, wherein said patient has suffered a traumatic injury of the lung.

In certain embodiments, the present invention relates to the aforementioned method, further comprising the step of collapsing the region of the lung.

In certain embodiments, the present invention relates to the aforementioned method, wherein said hydrogel is in contact with a mammalian tissue.

In certain embodiments, the present invention relates to the aforementioned method, wherein said hydrogel is in contact with a mammalian pulmonary tissue.

In certain embodiments, the present invention relates to the aforementioned method, wherein said hydrogel contacts an interior surface of a mammalian pulmonary tissue.

In certain embodiments, the present invention relates to the aforementioned method, wherein said hydrogel contacts an interior surface of a mammalian alveoli.

In certain embodiments, the present invention relates to the aforementioned method, wherein said hydrogel contacts an interior surface of a mammalian alveoli and partially or completely fills the mammalian alveoli.

In certain embodiments, the present invention relates to the aforementioned method, wherein said hydrogel comprises greater than about 80% water (w/w).

In certain embodiments, the present invention relates to the aforementioned method, wherein said hydrogel comprises greater than about 90% water (w/w).

In certain embodiments, the present invention relates to the aforementioned method, wherein said hydrogel comprises greater than about 95% water (w/w).

In certain embodiments, the present invention relates to the aforementioned method, wherein upon combination of said polymer, said crosslinker and said sclerosing agent, said hydrogel is formed in about 30 seconds.

In certain embodiments, the present invention relates to the aforementioned method, wherein upon combination of said polymer, said crosslinker and said sclerosing agent, said hydrogel is formed in about 1 minute.

In certain embodiments, the present invention relates to the aforementioned method, wherein upon combination of said polymer, said crosslinker and said sclerosing agent, said hydrogel is formed in about 2 minutes.

In certain embodiments, the present invention relates to the aforementioned method, wherein upon combination of said polymer, said crosslinker and said sclerosing agent, said hydrogel is formed in about 5 minutes.

In certain embodiments, the present invention relates to the aforementioned method, wherein upon combination of said polymer, said crosslinker and said sclerosing agent, said hydrogel is formed in about 15 minutes.

In certain embodiments, the present invention relates to the aforementioned method, wherein upon combination of said polymer, said crosslinker and said sclerosing agent, said hydrogel is formed in about 30 minutes.

In certain embodiments, the present invention relates to the aforementioned method, wherein said hydrogel degrades under physiological conditions in about 1 to about 12 weeks.

In certain embodiments, the present invention relates to the aforementioned method, wherein said hydrogel degrades under physiological conditions in about 1 to about 6 weeks.

In certain embodiments, the present invention relates to the aforementioned method, wherein said hydrogel degrades under physiological conditions in about 1 to about 4 weeks.

In certain embodiments, the present invention relates to the aforementioned method, wherein said hydrogel degrades under physiological conditions in about 2 to about 5 weeks.

In certain embodiments, the present invention relates to the aforementioned method, wherein said polymer comprises a plurality of 1,2-diols.

In certain embodiments, the present invention relates to the aforementioned method, wherein said 1,2-diols are cis-1,2-diols and are part of five-membered or six-membered rings.

In certain embodiments, the present invention relates to the aforementioned method, wherein said 1,2-diols are cis-1,2-diols and are part of six-membered rings.

In certain embodiments, the present invention relates to the aforementioned method, wherein said 1,2-diols are linear 1,2-diols.

In certain embodiments, the present invention relates to the aforementioned method, wherein said polymer comprises a plurality of 1,3-diols.

In certain embodiments, the present invention relates to the aforementioned method, wherein said 1,3-diols are cis-1,3-diols and are part of five-membered or six-membered rings.

In certain embodiments, the present invention relates to the aforementioned method, wherein said 1,3-diols are cis-1,3-diols and are part of six-membered rings.

In certain embodiments, the present invention relates to the aforementioned method, wherein said 1,3-diols are linear 1,3-diols.

In certain embodiments, the present invention relates to the aforementioned method, wherein said polymer is a polysaccharide comprising a cis-1,2-diol.

In certain embodiments, the present invention relates to the aforementioned method, wherein said polymer is guar gum, xanthan gum, an α-glucan, a galactomannan, or a glucomannan.

In certain embodiments, the present invention relates to the aforementioned method, wherein said polymer is selected from the group consisting of polyhydroxyethylmethacrylates, polyvinyl alcohols, polyacrylamides, poly-N-vinylpyrolidones, polyacrylic acids, polymethacrylic acids, polyethylene amines, and salts, esters, and copolymers thereof.

In certain embodiments, the present invention relates to the aforementioned method, wherein said polymer is polyvinyl alcohol.

In certain embodiments, the present invention relates to the aforementioned method, wherein said polyvinyl alcohol has a hydrolysis grade of greater than about 70.

In certain embodiments, the present invention relates to the aforementioned method, wherein said polyvinyl alcohol has a hydrolysis grade of greater than about 85.

In certain embodiments, the present invention relates to the aforementioned method, wherein said polyvinyl alcohol has a weight average molecular weight of between about 25,000 g/mol and about 250,000 g/mol.

In certain embodiments, the present invention relates to the aforementioned method, wherein said polyvinyl alcohol has a weight average molecular weight of between about 50,000 g/mol and about 150,000 g/mol.

In certain embodiments, the present invention relates to the aforementioned method, wherein said polyvinyl alcohol has a weight average molecular weight of about 100,000 g/mol.

In certain embodiments, the present invention relates to the aforementioned method, wherein said polymer is copolymer of a first monomer and a second monomer; wherein said first monomer is a polyvinyl alcohol-yielding monomer; and said second monomer is selected from the group consisting of olefins, propylene, 1-butene, isobutene, acrylic acid, acrylic acid salts, acrylates, methyl acrylate, ethyl acrylate, n-propyl acrylate, i-propyl acrylate, n-butyl acrylate, i-butyl acrylate, t-butyl acrylate, 2-ethylhexyl acrylate, dodecyl acrylate, octadecyl acrylate, methacrylic acid, methacrylic acid salts, methacrylates, methyl methacrylate, ethyl methacrylate, n-propyl methacrylate, i-propyl methacrylate, n-butyl methacrylate, i-butyl methacrylate, t-butyl methacrylate, 2-ethylhexyl methacrylate, dodecyl methacrylate, octadecyl methacrylate, acrylamide, N-methylacrylamide, N-ethylacrylamide, N,N-dimethylacrylamide, diacetonacrylamide, acrylamidopropanesulfonic acid, salts of acrylamidopropanesulfonic acid, acrylamidopropyldimethylamine, salts of acrylamidopropyldimethylamine, N-methylolacrylamide, methacrylamide, N-methylmethacrylamide, N-ethylmethacrylamide, methacrylamidopropanesulfonic acid, salts of methacrylamidopropanesulfonic acid, methacrylamidopropyldimethylamine, salts of methacrylamidopropyldimethylamine, N-methylolmethacrylamide, N-vinylamides, N-vinylformamide, N-vinylacetamide, N-vinylpyrrolidone, vinyl ethers, methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether, nitriles, acrylonitrile, methacrylonitrile, vinyl halides, vinyl chloride, vinylidene chloride, vinyl fluoride, vinylidene fluoride, allyl compounds, allyl acetate, allyl chloride, maleic acid, salts of maleic acid, maleic acid esters, itaconic acid, salts of itaconic acid, itaconic acid esters, vinylsilyl compounds, vinyltrimethoxysilane, isopropenyl acetate, N-vinylamides, N-vinylformamide, N-vinylacetamide, and N-vinylpyrrolidone.

In certain embodiments, the present invention relates to the aforementioned method, wherein said copolymer is a block copolymer, random copolymer, graft polymer, or branched copolymer.

In certain embodiments, the present invention relates to the aforementioned method, wherein said copolymer comprises about 50 mol % of the first monomer.

In certain embodiments, the present invention relates to the aforementioned method, wherein said copolymer comprises about 60 mol % of the first monomer.

In certain embodiments, the present invention relates to the aforementioned method, wherein said copolymer comprises about 70 mol % of the first monomer.

In certain embodiments, the present invention relates to the aforementioned method, wherein said copolymer comprises about 80 mol % of the first monomer.

In certain embodiments, the present invention relates to the aforementioned method, wherein said copolymer comprises about 90 mol % of the first monomer.

In certain embodiments, the present invention relates to the aforementioned method, wherein said copolymer comprises about 95 mol % of the first monomer.

In certain embodiments, the present invention relates to the aforementioned method, wherein said crosslinker is water soluble at a concentration of at least about 1 mg/mL.

In certain embodiments, the present invention relates to the aforementioned method, wherein said crosslinker is water soluble at a concentration of at least about 2.5 mg/mL.

In certain embodiments, the present invention relates to the aforementioned method, wherein said crosslinker is water soluble at a concentration of at least about 5 mg/mL.

In certain embodiments, the present invention relates to the aforementioned method, wherein said crosslinker is water soluble at a concentration of at least about 10 mg/mL.

In certain embodiments, the present invention relates to the aforementioned method, wherein said crosslinker is water soluble at a concentration of at least about 20 mg/mL.

In certain embodiments, the present invention relates to the aforementioned method, wherein said crosslinker is derived from a compound selected from the group consisting of boric acid, borates, boronic acids, boronates and boroxines.

In certain embodiments, the present invention relates to the aforementioned method, wherein said crosslinker is derived from boric acid or a borate.

In certain embodiments, the present invention relates to the aforementioned method, wherein said crosslinker is derived from boric acid, sodium borate or potassium borate.

In certain embodiments, the present invention relates to the aforementioned method, wherein said crosslinker is derived from a boronic acid, a boronate, or a boroxine.

In certain embodiments, the present invention relates to the aforementioned method, wherein said crosslinker is derived from compounds selected from the group consisting of alkyl boronic acids, alkyl boronates, alkyl boroxine, alkenyl boronic acids, alkenyl boronates, alkenyl boroxine, aryl boronic acids, aryl boronates, aryl boroxine, heteroaryl boronic acids, heteroaryl boronates, heteroaryl boroxine, aralkyl boronic acid, aralkyl boronates, aralkyl boroxine, heteroaralkyl boronic acids, heteroaralkyl boronates and heteroaralkyl boroxine.

In certain embodiments, the present invention relates to the aforementioned method, wherein said crosslinker is derived from an optionally-substituted phenyl boronic acid, an optionally-substituted phenyl boronate, or an optionally-substituted phenyl boroxine.

In certain embodiments, the present invention relates to the aforementioned method, wherein said crosslinker is derived from compounds selected from the group consisting of trans-2-phenylvinylboronic acid, trans-2-(4-chlorophenyl)vinylboronic acid, trans-2-(4-fluorophenyl)vinylboronic acid, trans-2-(4-methoxyphenyl)vinylboronic acid, trans-2-(4-(trifluoromethyl)phenyl)vinylboronic acid, trans-1-hexen-1-ylboronic acid, trans-1-octen-1-ylboronic acid, trans-2-[3-(trifluoromethyl)phenyl]vinylboronic acid, trans-2-(4-biphenyl)vinylboronic acid, trans-2-(3-methoxyphenyl)vinylboronic acid, trans-2-chloromethylvinylboronic acid, (ε)-5-chloro-1-penteneboronic acid, trans-2-(4-methylphenyl)vinylboronic acid, α-phenyl vinylboronic acid, cis-propenylboronic acid, trans-propenylboronic acid, 1-pentenylboronic acid, 2-cyclohexylvinylboronic acid, 1-benzothiophen-2-ylboronic acid, n-boc-2-pyrryl-boronic acid, 2-thienylboronic acid, thiophene-3-boronic acid, 2-furanboronic acid, 2,5-thiophenediboronic acid, 2-formyl-3-thiopheneboronic acid, 3-formyl-2-thiopheneboronic acid, 5-acetyl-2-thiopheneboronic acid, 5-chloro-2-thienylboronic acid, benzofuran-2-ylboronic acid, 4-dibenzofuranboronic acid, benzothiophen-2- ylboronic acid, 4-dibenzothiopheneboronic acid, thianaphthene-3-boronic acid, 3-pyridineboronic acid, 3-furanboronic acid, 5-methyl-2-thiopheneboronic acid, thianthrene-1-boronic acid, 5-methyl-2-furanboronic acid, 5-formyl-2-furanboronic acid, 5-formyl-2-thiopheneboronic acid, 4-methyl-3-thiopheneboronic acid, 5-bromothiophene-2-boronic acid, N-Boc-indole-2-boronic acid, 1-(phenylsulfonyl)-2-indoleboronic acid, 1-(phenylsulfonyl)-3-indoleboronic acid, 4-pyridineboronic acid, 2-chloro-5-pyridineboronic acid, 3-aminophenylboronic acid monohydrate, 3-nitrophenylboronic acid, o-tolylboronic acid, m-tolylboronic acid, p-tolylboronic acid, 3-aminophenylboronic acid hydrochloride, π-phenylenediboronic acid, 3-chlorophenylboronic acid, 4-chlorophenylboronic acid, 4-fluorophenylboronic acid, 4-vinylphenylboronic acid, 4-methoxyphenylboronic acid, 2-formylphenylboronic acid, 4-formylphenylboronic acid, 3-(trifluoromethyl)phenylboronic acid, 4-(trifluoromethyl)phenylboronic acid, 3-bromophenylboronic acid, 3-ethoxyphenylboronic acid, 3-fluorophenylboronic acid, 3-formylphenylboronic acid, 3-iodophenylboronic acid, 3-methoxyphenylboronic acid, 2-(trifluoromethyl)phenylboronic acid, 3,5-dichlorophenylboronic acid, 2-chlorophenylboronic acid, 2-fluorophenylboronic acid, 2-methoxyphenylboronic acid, 2-ethoxyphenylboronic acid, 4-ethoxyphenylboronic acid, 3-carboxyphenylboronic acid, 4-carboxyphenylboronic acid, 4,4'-biphenyldiboronic acid, 4-(methylthio)phenylboronic acid, 2,4-difluorophenylboronic acid, 3,4-difluorophenylboronic acid, pentafluorophenylboronic acid, 2,6-difluorophenylboronic acid, 2-acetylphenylboronic acid, 3-acetylphenylboronic acid, 4-acetylphenylboronic acid, 3,5-bis(trifluoromethyl)phenylboronic acid, 3,4-dichlorophenylboronic acid, 3,5-difluorophenylboronic acid, 4-iodophenylboronic acid, 2-bromophenylboronic acid, 4-tert-butylphenylboronic acid, 2,6-dimethylphenylboronic acid, 3,5-dimethylphenylboronic acid, 2,6-dimethoxyphenylboronic acid, 3,4-dimethoxyphenylboronic acid, naphthalene-2-boronic acid, 2-naphthylboronic acid, 4-phenoxyphenylboronic acid, 4-biphenylboronic acid, 2,4-dimethoxyphenylboronic acid, 2,5-dimethoxyphenylboronic acid, 2,3-dimethylphenylboronic acid, 2,5-dimethylphenylboronic acid, 4-(dimethylamino)phenylboronic acid, 5-fluoro-2-methoxyphenylboronic acid, 4-fluoro-3-methylphenylboronic acid, 3,5-dibromophenylboronic acid, 4-ethylphenylboronic acid, 3,4-(methylenedioxy)phenylboronic acid, 3-(trifluoromethoxy)phenylboronic acid, 4-(trifluoromethoxy)phenylboronic acid, 2-fluoro-4-biphenylylboronic acid, 3-chloro-4-fluorophenylboronic acid, 5-chloro-2-methoxyphenylboronic acid, 5-formyl-2-methoxyphenylboronic acid, 2,3,4-trimethoxyphenylboronic acid, 2,5-dichlorophenylboronic acid, 4-(hydroxymethyl)phenylboronic acid, 4-borono-dl-phenylalanine, 5-bromo-2-methoxyphenylboronic acid, 2-chloro-6-methoxyphenylboronic acid, 2-fluoro-6-methoxyphenylboronic acid, 5-bromo-2-ethoxyphenylboronic acid, 3-(hydroxymethyl)phenylboronic acid, 3-formyl-4-methoxyphenylboronic acid, 3-cyanophenylboronic acid, 2,5-difluorophenylboronic acid, 2,3-difluorophenylboronic acid, 2,3-dichlorophenylboronic acid, 2-(methylthio)phenylboronic acid, 2-benzyloxyphenylboronic acid, 2,4-dichlorophenylboronic acid, 2-cyanophenylboronic acid, 4-cyanophenylboronic acid, 4-methyl-1-naphthaleneboronic acid, 4-methyl-3-nitrophenylboronic acid, 2-phenoxyphenylboronic acid, 4-butylphenylboronic acid, 4-propylphenylboronic acid, 2-ethylphenylboronic acid, 2-ethoxy-1-naphthaleneboronic acid, 6-methoxy-2-naphthaleneboronic acid, 6-ethoxy-2-naphthaleneboronic acid, 3-(trimethylsilyl)phenylboronic acid, 4-(trimethylsilyl)phenylboronic acid, 3-hydroxyphenylboronic acid, 4-hydroxyphenylboronic acid, 3-mercaptophenylboronic acid, 4-mercaptophenylboronic acid, 3-(tert-butyldimethylsilyoxy)phenylboronic acid, 2,3,4-trifluorophenylboronic acid, 2,3,6-trifluorophenylboronic acid, 2,4,6-trifluorophenylboronic acid, 2,4,5-trifluorophenylboronic acid, 2,3,5-trifluorophenylboronic acid, 3,4,5-trifluorophenylboronic acid, 4-benzoylphenylboronic acid, 3-benzyloxyphenylboronic acid, 3-biphenylboronic acid, 2-biphenylboronic acid, 3-fluoro-4-formylphenylboronic acid, 2,4,6-trimethylphenylboronic acid, 2,4,5-trimethylphenylboronic acid, 3-isopropoxyphenylboronic acid, 2-isopropoxyphenylboronic acid, 4-isopropoxyphenylboronic acid, 2-butoxyphenylboronic acid, 3-butoxyphenylboronic acid, 4-butoxyphenylboronic acid, 3-bromo-2-ethoxy-5-fluorophenylboronic acid, 5-chloro-2-ethoxyphenylboronic acid, 1-pyreneboronic acid, 4-bromo-2,6-difluorophenylboronic acid, 3-chloro-2-fluorophenylboronic acid, 5-chloro-2-fluorophenylboronic acid, 3-bromo-2,6-difluorophenylboronic acid, 2-chloro-6-fluoro-3-methylphenylboronic acid, 2-chloro-6-fluoro-5-methylphenylboronic acid, 5-chloro-2-fluoro-3-methylphenylboronic acid, 4-propoxyphenylboronic acid, 3-propoxyphenylboronic acid, 2-propoxyphenylboronic acid, 2,3-dimethoxyphenylboronic acid, 2-fluoro-5-(trifluoromethyl)phenylboronic acid, 3-bromo-2-fluorophenylboronic acid, 3-fluoro-4-methoxyphenylboronic acid, 4-ethoxy-3-fluorophenylboronic acid, 3-fluoro-4-isopropoxyphenylboronic acid, 4-butoxy-3-chlorophenylboronic acid, 3-chloro-4-isopropoxyphenylboronic acid, 3-chloro-4-propoxyphenylboronic acid, 3-chloro-4-ethoxyphenylboronic acid, 3-chloro-4-methoxyphenylboronic acid, 2-butoxy-5-fluorophenylboronic acid, 5-fluoro-2-isopropoxyphenylboronic acid, 5-methyl-2-propoxyphenylboronic acid, 4-fluoro-2-methylphenylboronic acid, 2-isopropoxy-5-methylphenylboronic acid, 2-butoxy-5-methylphenylboronic acid, 5-fluoro-2-propoxyphenylboronic acid, 4-acetamidophenylboronic acid, 4-(n-boc-amino)phenylboronic acid, 3-acetamidophenylboronic acid, 2-chloro-6-fluorophenylboronic acid, 9,9-dihexylfluorene-2,7-dioronic acid, 2-fluoro-4-methylphenylboronic acid, 3-fluoro-4-methylphenylboronic acid, 2-fluoro-5-methylphenylboronic acid, acenaphthene-5-boronic acid, 3,5-diformylphenylboronic acid, 2-ethoxy-5-methylphenylboronic acid, 2-methoxy-5-methylphenylboronic acid, 9,9-dioctylfluorene-2,7-diboronic acid, 2,3-difluoro-4-formylphenylboronic acid, 9,9-didodecylfluorene-2,7-diboronic acid, 9,9-di(2'-ethylhexyl)fluorene-2,7-diboronic acid, 4-ethoxycarbonylphenylboronic acid, 3-ethoxycarbonylphenylboronic acid, n-(4-phenylboronic)succinamic acid, 3-methoxycarbonylphenylboronic acid, 3-bromo-2-butoxyphenylboronic acid, 2,6-difluoro-4-methoxyphenylboronic acid, 2-fluoro-5-iodophenylboronic acid, 2-fluoro-3-iodophenylboronic acid, 5-bromo-2-fluorophenylboronic acid, 2-bromo-6-fluorophenylboronic acid, 4-bromo-2,3,5,6-tetrafluorophenylboronic acid, 2-fluoro-3-methoxyphenylboronic acid, 2-fluoro-3-methoxyphenylboronic acid, 2-fluoro-5-propoxyphenylboronic acid, 5-ethoxy-2-fluorophenylboronic acid, 2-ethoxy-6-fluorophenylboronic acid, 4-methoxycarbonylpheynlboronic acid, 4-butoxy-2-methylphenylboronic acid, 4-ethoxy-2-methylphenylboronic acid, 2-ethoxy-5-fluorophenylboronic acid, 4-methoxy-3-methylphenylboronic acid, 4-benzyloxy-3-chlorophenylboronic acid, 3-bromo-5-methyl-2- methoxyphenylboronic acid, 3-bromo-2-ethoxy-5-methylphenylboronic acid, 3-bromo-2-isopropoxy-5-methylphenylboronic acid, 3-bromo-5-methyl-2-propoxyphenylboronic acid, 3-bromo-2-butoxy-5-methylphenylboronic acid, 3-bromo-2-propoxyphenylboronic acid, 2-fluoro-5-methoxyphenylboronic acid, 3-bromo-2-isopropoxyphenylboronic acid, 3-(ethylthio)phenylboronic acid, 2,4-difluoro-3-formylphenylboronic acid, 4-butoxy-3,5-dimethylphenylboronic acid, 3,5-dimethyl-4-propoxyphenylboronic acid, 3,5-dimethyl-4-ethoxyphenylboronic acid, 3,5-dimethyl-4-methoxyphenylboronic acid, 3-benzyloxy-2,6-difluorophenylboronic acid, 3-(2'-chlorobenzyloxy)phenylboronic acid, 4-(3',5'-dimethoxybenzyloxy)phenylboronic acid, 3-(3',5'-dimethoxybenzyloxy)phenylboronic acid, 2-bromo-5,6-difluorophenylboronic acid, 2-fluoro-6-propoxyphenylboronic acid, 2-benzyloxy-3-bromo-5-methylphenylboronic acid, 2-(2'-chlorobenzyloxy)phenylboronic acid, 3-aminophenylboronic acid, 4-bromophenylboronic acid, 1-naphthylboronic acid, phenylboronic acid, butylboronic acid, methylboronic acid, (2-methylpropyl)boronic acid, and the corresponding boronates and boroxines thereof.

In certain embodiments, the present invention relates to the aforementioned method, wherein said crosslinker is derived from a bis-boronic acid or a bis-boronate.

In certain embodiments, the present invention relates to the aforementioned method, wherein said sclerosing agent is water soluble at a concentration of at least about 1 mg/mL.

In certain embodiments, the present invention relates to the aforementioned method, wherein said sclerosing agent is water soluble at a concentration of at least about 2.5 mg/mL.

In certain embodiments, the present invention relates to the aforementioned method, wherein said sclerosing agent is water soluble at a concentration of at least about 5 mg/mL.

In certain embodiments, the present invention relates to the aforementioned method, wherein said sclerosing agent is water soluble at a concentration of at least about 10 mg/mL.

In certain embodiments, the present invention relates to the aforementioned method, wherein said sclerosing agent is water soluble at a concentration of at least about 20 mg/mL.

In certain embodiments, the present invention relates to the aforementioned method, wherein said sclerosing agent comprises a polycation.

In certain embodiments, the present invention relates to the aforementioned method, wherein said polycation is a polyamine, a polysaccharide, or a polyamino acid.

In certain embodiments, the present invention relates to the aforementioned method, wherein said polycation is a polysaccharide or a polyamino acid.

In certain embodiments, the present invention relates to the aforementioned method, wherein said polycation is polylysine, polyarginine, polyomithine, chitosan polycations, gelatin polycations, or albumin polycations.

In certain embodiments, the present invention relates to the aforementioned method, wherein said polycation is a poly(amino acid), wherein said poly(amino acid) comprises a plurality of amino acids independently selected from the group consisting of Lys and Arg; and a plurality of amino acids independently selected from the group consisting of Gly, Ala, Val, Leu, Ile, Met, Pro, Phe, Trp, Asn, Gln, Ser, Thr, Tyr, Cys, and His; provided that no less than twenty-five percent of the amino acids is independently selected from the group consisting of Lys and Arg; further provided that no more than five percent of the amino acids is independently selected from the group consisting of Asp and Glu.

In certain embodiments, the present invention relates to the aforementioned method, wherein said polycation is a poly(amino acid), wherein said poly(amino acid) is represented by poly(X-Y), poly(X-Y-Y), or poly(X-Y-Y-Y), wherein X is independently for each occurrence Lys or Arg; and Y is independently for each occurrence Gly, Ala, Val, Leu, Ile, Met, Pro, Phe, Trp, Asn, Gln, Ser, Thr, Tyr, Cys, or His.

In certain embodiments, the present invention relates to the aforementioned method, wherein said polycation is poly-L-lysine.

In certain embodiments, the present invention relates to the aforementioned method, wherein said polycation degrades under physiological conditions in about 1 to about 12 weeks.

In certain embodiments, the present invention relates to the aforementioned method, wherein said polycation degrades under physiological conditions in about 1 to about 6 weeks.

In certain embodiments, the present invention relates to the aforementioned method, wherein said polycation degrades under physiological conditions in about 1 to about 4 weeks.

In certain embodiments, the present invention relates to the aforementioned method, wherein said polycation degrades under physiological conditions in about 2 to about 5 weeks.

In certain embodiments, the present invention relates to the aforementioned method, wherein said fourth amount of said polyanion is present in said third mixture.

In certain embodiments, the present invention relates to the aforementioned method, wherein said polyanion is a polysaccharide or a polyamino acid.

In certain embodiments, the present invention relates to the aforementioned method, wherein said polyanion is selected from the group consisting of sodium alginate gelatin polyanions, hyaluronic acid, carrageenan, chondroitin sulfate, carboxymethylcellulose, polyglutamic acid, and polyaspartic acid.

In certain embodiments, the present invention relates to the aforementioned method, wherein said polyanion is chondroitin sulfate.

In certain embodiments, the present invention relates to the aforementioned method, wherein said polyanion degrades under physiological conditions in about 1 to about 12 weeks.

In certain embodiments, the present invention relates to the aforementioned method, wherein said polyanion degrades under physiological conditions in about 1 to about 6 weeks.

In certain embodiments, the present invention relates to the aforementioned method, wherein said polyanion degrades under physiological conditions in about 1 to about 4 weeks.

In certain embodiments, the present invention relates to the aforementioned method, wherein said polyanion degrades under physiological conditions in about 2 to about 5 weeks.

In certain embodiments, the present invention relates to the aforementioned method, wherein the ratio of the product of the mass of the polycation and the charge per mass ratio of the polycation to the product of the mass of the polyanion and the charge per mass ratio of the polyanion is greater than about 1.

In certain embodiments, the present invention relates to the aforementioned method, wherein the ratio of the product of the mass of the polycation and the charge per mass ratio of the polycation to the product of the mass of the polyanion and the charge per mass ratio of the polyanion is greater than about 1 and less than about 20.

In certain embodiments, the present invention relates to the aforementioned method, wherein the ratio of the product of the mass of the polycation and the charge per mass ratio of the polycation to the product of the mass of the polyanion and the charge per mass ratio of the polyanion is greater than about 5 and less than about 10.

In certain embodiments, the present invention relates to the aforementioned method, wherein the polycation and the polyanion form a precipitated complex.

In certain embodiments, the present invention relates to the aforementioned method, wherein said sclerosing agent is a peroxide.

In certain embodiments, the present invention relates to the aforementioned method, wherein said peroxide is hydrogen peroxide, a peroxyborate, a peroxyboric acid, a peroxycarbonate, a peroxycarbonic acid, an alkyl hydroperoxide, an aryl hydroperoxide, an aralkyl hydroperoxide, a peroxyacetate, or a peroxyacetic acid.

In certain embodiments, the present invention relates to the aforementioned method, wherein said peroxide is sodium perborate, sodium percarbonate, or sodium peracetate.

In certain embodiments, the present invention relates to the aforementioned method, further comprising the step of co-administering to said patient a fifth amount of an anti-infective.

In certain embodiments, the present invention relates to the aforementioned method, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned method, wherein said anti-infective is tetracycline.

In certain embodiments, the present invention relates to the aforementioned method, further comprising the step of co-administering to said patient a sixth amount of a contrast-enhancing agent.

In certain embodiments, the present invention relates to the aforementioned method, wherein said contrast-enhancing agent is selected from the group consisting of radiopaque materials, paramagnetic materials, heavy atoms, transition metals, lanthanides, actinides, dyes, and radionuclide-containing materials.

SELECTED KITS OF THE INVENTION. This invention also provides kits for conveniently and effectively implementing the methods of this invention. Such kits comprise any of the polymers, crosslinkers and/or sclerosing agents of the present invention or a combination thereof, and a means for facilitating their use consistent with methods of this invention. Such kits provide a convenient and effective means for assuring that the methods are practiced in an effective manner. The compliance means of such kits includes any means which facilitates practicing a method of this invention. Such compliance means include instructions, packaging, and dispensing means, and combinations thereof. Kit components may be packaged for either manual or partially or wholly automated practice of the foregoing methods. In other embodiments, this invention contemplates a kit including polymers, crosslinkers and/or sclerosing agents of the present invention, and optionally instructions for their use.

Any of these kits can contain devices used in non-surgical lung volume reduction. For example, they can also contain a catheter (e.g., a single- or multi-lumen (e.g., dual-lumen) catheter that, optionally, includes a balloon or other device suitable for inhibiting airflow within the respiratory tract), tubing or other conduits for removing material (e.g., solutions, including those that carry debrided epithelial cells) from the lung, a stent or a valve or other device that may be placed in an airway to block or reduce airflow into or out of a lung or lung region, and/or a bronchoscope.

One aspect of the invention relates to a kit, comprising: a first container comprising a first amount of a first mixture comprising a polymer containing a plurality of pendent hydroxyl groups; a second container comprising a second amount of a second mixture comprising a crosslinker; a third container comprising a third amount of a third mixture comprising a sclerosing agent and optionally comprising a fourth amount of a polyanion; and instructions for use thereof in lung volume reduction therapy.

In certain embodiments, the present invention relates to the aforementioned kit, wherein said hydrogel formed by the combination of said first, second and third containers further comprises a gas.

In certain embodiments, the present invention relates to the aforementioned kit, wherein said hydrogel formed by the combination of said first, second and third containers further comprises oxygen.

In certain embodiments, the present invention relates to the aforementioned kit, wherein said hydrogel formed by the combination of said first, second and third containers comprises greater than about 80% water (w/w).

In certain embodiments, the present invention relates to the aforementioned kit, wherein said hydrogel formed by the combination of said first, second and third containers comprises greater than about 90% water (w/w).

In certain embodiments, the present invention relates to the aforementioned kit, wherein said hydrogel formed by the combination of said first, second and third containers comprises greater than about 95% water (w/w).

In certain embodiments, the present invention relates to the aforementioned kit, wherein upon combination of said polymer, said crosslinker and said sclerosing agent, a hydrogel is formed in about 30 seconds.

In certain embodiments, the present invention relates to the aforementioned kit, wherein upon combination of said polymer, said crosslinker and said sclerosing agent, a hydrogel is formed in about 1 minute.

In certain embodiments, the present invention relates to the aforementioned kit, wherein upon combination of said polymer, said crosslinker and said sclerosing agent, a hydrogel is formed in about 2 minutes.

In certain embodiments, the present invention relates to the aforementioned kit, wherein upon combination of said polymer, said crosslinker and said sclerosing agent, a hydrogel is formed in about 5 minutes.

In certain embodiments, the present invention relates to the aforementioned kit, wherein upon combination of said polymer, said crosslinker and said sclerosing agent, a hydrogel is formed in about 15 minutes.

In certain embodiments, the present invention relates to the aforementioned kit, wherein upon combination of said polymer, said crosslinker and said sclerosing agent, a hydrogel is formed in about 30 minutes.

In certain embodiments, the present invention relates to the aforementioned kit, wherein said hydrogel formed by the combination of said first, second and third containers degrades under physiological conditions in about 1 to about 12 weeks.

In certain embodiments, the present invention relates to the aforementioned kit, wherein said hydrogel formed by the combination of said first, second and third containers degrades under physiological conditions in about 1 to about 6 weeks.

In certain embodiments, the present invention relates to the aforementioned kit, wherein said hydrogel formed by the combination of said first, second and third containers degrades under physiological conditions in about 1 to about 4 weeks.

In certain embodiments, the present invention relates to the aforementioned kit, wherein said hydrogel formed by the combination of said first, second and third containers degrades under physiological conditions in about 2 to about 5 weeks.

In certain embodiments, the present invention relates to the aforementioned kit, wherein said polymer comprises a plurality of 1,2-diols.

In certain embodiments, the present invention relates to the aforementioned kit, wherein said 1,2-diols are cis-1,2-diols and are part of five-membered or six-membered rings.

In certain embodiments, the present invention relates to the aforementioned kit, wherein said 1,2-diols are cis-1,2-diols and are part of six-membered rings.

In certain embodiments, the present invention relates to the aforementioned kit, wherein said 1,2-diols are linear 1,2-diols.

In certain embodiments, the present invention relates to the aforementioned kit, wherein said polymer comprises a plurality of 1,3-diols.

In certain embodiments, the present invention relates to the aforementioned kit, wherein said 1,3-diols are cis-1,3-diols and are part of five-membered or six-membered rings.

In certain embodiments, the present invention relates to the aforementioned kit, wherein said 1,3-diols are cis-1,3-diols and are part of six-membered rings.

In certain embodiments, the present invention relates to the aforementioned kit, wherein said 1,3-diols are linear 1,3-diols.

In certain embodiments, the present invention relates to the aforementioned kit, wherein said polymer is a polysaccharide comprising a cis-1,2-diol.

In certain embodiments, the present invention relates to the aforementioned kit, wherein said polymer is guar gum, xanthan gum, an α-glucan, a galactomannan, or a glucomannan.

In certain embodiments, the present invention relates to the aforementioned kit, wherein said polymer is selected from the group consisting of polyhydroxyethylmethacrylates, polyvinyl alcohols, polyacrylamides, poly-N-vinylpyrrolidones, polyacrylic acids, polymethacrylic acids, polyethylene amines, and salts, esters, and copolymers thereof.

In certain embodiments, the present invention relates to the aforementioned kit, wherein said polymer is polyvinyl alcohol.

In certain embodiments, the present invention relates to the aforementioned kit, wherein said polyvinyl alcohol has a hydrolysis grade of greater than about 70.

In certain embodiments, the present invention relates to the aforementioned kit, wherein said polyvinyl alcohol has a hydrolysis grade of greater than about 85.

In certain embodiments, the present invention relates to the aforementioned kit, wherein said polyvinyl alcohol has a weight average molecular weight of between about 25,000 g/mol and about 250,000 g/mol.

In certain embodiments, the present invention relates to the aforementioned kit, wherein said polyvinyl alcohol has a weight average molecular weight of between about 50,000 g/mol and about 150,000 g/mol.

In certain embodiments, the present invention relates to the aforementioned kit, wherein said polyvinyl alcohol has a weight average molecular weight of about 100,000 g/mol.

In certain embodiments, the present invention relates to the aforementioned kit, wherein said polymer is copolymer of a first monomer and a second monomer; wherein said first monomer is a polyvinyl alcohol-yielding monomer; and said second monomer is selected from the group consisting of olefins, propylene, 1-butene, isobutene, acrylic acid, acrylic acid salts, acrylates, methyl acrylate, ethyl acrylate, n-propyl acrylate, i-propyl acrylate, n-butyl acrylate, i-butyl acrylate, t-butyl acrylate, 2-ethylhexyl acrylate, dodecyl acrylate, octadecyl acrylate, methacrylic acid, methacrylic acid salts, methacrylates, methyl methacrylate, ethyl methacrylate, n-propyl methacrylate, i-propyl methacrylate, n-butyl methacrylate, i-butyl methacrylate, t-butyl methacrylate, 2-ethylhexyl methacrylate, dodecyl methacrylate, octadecyl methacrylate, acrylamide, N-methylacrylamide, N-ethylacrylamide, N,N-dimethylacrylamide, diacetonacrylamide, acrylamidopropanesulfonic acid, salts of acrylamidopropanesulfonic acid, acrylamidopropyldimethylamine, salts of acrylamidopropyldimethylamine, N-methylolacrylamide, methacrylamide, N-methylmethacrylamide, N-ethylmethacrylamide, methacrylamidopropanesulfonic acid, salts of methacrylamidopropanesulfonic acid, methacrylamidopropyldimethylamine, salts of methacrylamidopropyldimethylamine, N-methylolmethacrylamide, N-vinylamides, N-vinylformamide, N-vinylacetamide, N-vinylpyrrolidone, vinyl ethers, methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether, nitriles, acrylonitrile, methacrylonitrile, vinyl halides, vinyl chloride, vinylidene chloride, vinyl fluoride, vinylidene fluoride, allyl compounds, allyl acetate, allyl chloride, maleic acid, salts of maleic acid, maleic acid esters, itaconic acid, salts of itaconic acid, itaconic acid esters, vinylsilyl compounds, vinyltrimethoxysilane, isopropenyl acetate, N-vinylamides, N-vinylformamide, N-vinylacetamide, and N-vinylpyrrolidone.

In certain embodiments, the present invention relates to the aforementioned kit, wherein said copolymer is a block copolymer, random copolymer, graft polymer, or branched copolymer.

In certain embodiments, the present invention relates to the aforementioned kit, wherein said copolymer comprises about 50 mol % of the first monomer.

In certain embodiments, the present invention relates to the aforementioned kit, wherein said copolymer comprises about 60 mol % of the first monomer.

In certain embodiments, the present invention relates to the aforementioned kit, wherein said copolymer comprises about 70 mol % of the first monomer.

In certain embodiments, the present invention relates to the aforementioned kit, wherein said copolymer comprises about 80 mol % of the first monomer.

In certain embodiments, the present invention relates to the aforementioned kit, wherein said copolymer comprises about 90 mol % of the first monomer.

In certain embodiments, the present invention relates to the aforementioned kit, wherein said copolymer comprises about 95 mol % of the first monomer.

In certain embodiments, the present invention relates to the aforementioned kit, wherein said crosslinker is water soluble at a concentration of at least about 1 mg/mL.

In certain embodiments, the present invention relates to the aforementioned kit, wherein said crosslinker is water soluble at a concentration of at least about 2.5 mg/mL.

In certain embodiments, the present invention relates to the aforementioned kit, wherein said crosslinker is water soluble at a concentration of at least about 5 mg/mL.

In certain embodiments, the present invention relates to the aforementioned kit, wherein said crosslinker is water soluble at a concentration of at least about 10 mg/mL.

In certain embodiments, the present invention relates to the aforementioned kit, wherein said crosslinker is water soluble at a concentration of at least about 20 mg/mL.

In certain embodiments, the present invention relates to the aforementioned kit, wherein said crosslinker is derived from a compound selected from the group consisting of boric acid, borates, boronic acids, boronates and boroxines.

In certain embodiments, the present invention relates to the aforementioned kit, wherein said crosslinker is derived from boric acid or a borate.

In certain embodiments, the present invention relates to the aforementioned kit, wherein said crosslinker is derived from boric acid, sodium borate or potassium borate.

In certain embodiments, the present invention relates to the aforementioned kit, wherein said crosslinker is derived from a boronic acid, a boronate, or a boroxine.

In certain embodiments, the present invention relates to the aforementioned kit, wherein said crosslinker is derived from compounds selected from the group consisting of alkyl boronic acids, alkyl boronates, alkyl boroxine, alkenyl boronic acids, alkenyl boronates, alkenyl boroxine, aryl boronic acids, aryl boronates, aryl boroxine, heteroaryl boronic acids, heteroaryl boronates, heteroaryl boroxine, aralkyl boronic acid, aralkyl boronates, aralkyl boroxine, heteroaralkyl boronic acids, heteroaralkyl boronates and heteroaralkyl boroxine.

In certain embodiments, the present invention relates to the aforementioned kit, wherein said crosslinker is derived from an optionally-substituted phenyl boronic acid, an optionally-substituted phenyl boronate, or an optionally-substituted phenyl boroxine.

In certain embodiments, the present invention relates to the aforementioned kit, wherein said crosslinker is derived from compounds selected from the group consisting of trans-2-phenylvinylboronic acid, trans-2-(4-chlorophenyl)vinylboronic acid, trans-2-(4-fluorophenyl)vinylboronic acid, trans-2-(4-methoxyphenyl)vinylboronic acid, trans-2-(4-(trifluoromethyl)phenyl)vinylboronic acid, trans-1-hexen-1-ylboronic acid, trans-1-octen-1-ylboronic acid, trans-2-[3-(trifluoromethyl)phenyl]vinylboronic acid, trans-2-(4-biphenyl)vinylboronic acid, trans-2-(3-methoxyphenyl)vinylboronic acid, trans-2-chloromethylvinylboronic acid, (ε)-5-chloro-1-penteneboronic acid, trans-2-(4-methylphenyl)vinylboronic acid, α-phenyl vinylboronic acid, cis-propenylboronic acid, trans-propenylboronic acid, 1-pentenyl-boronic acid, 2-cyclohexylvinylboronic acid, 1-benzothiophen-2-ylboronic acid, n-boc-2-pyrryl-boronic acid, 2-thienylboronic acid, thiophene-3-boronic acid, 2-furanboronic acid, 2,5-thiophenediboronic acid, 2-formyl-3-thiopheneboronic acid, 3-formyl-2-thiopheneboronic acid, 5-acetyl-2-thiopheneboronic acid, 5-chloro-2-thienylboronic acid, benzofuran-2-ylboronic acid, 4-dibenzofuranboronic acid, benzothiophen-2-ylboronic acid, 4-dibenzothiopheneboronic acid, thianaphthene-3-boronic acid, 3-pyridineboronic acid, 3-furanboronic acid, 5-methyl-2-thiopheneboronic acid, thianthrene-1-boronic acid, 5-methyl-2-furanboronic acid, 5-formyl-2-furanboronic acid, 5-formyl-2-thiopheneboronic acid, 4-methyl-3-thiopheneboronic acid, 5-bromothiophene-2-boronic acid, N-Boc-indole-2-boronic acid, 1-(phenylsulfonyl)-2-indoleboronic acid, 1-(phenylsulfonyl)-3-indoleboronic acid, 4-pyridineboronic acid, 2-chloro-5-pyridineboronic acid, 3-aminophenylboronic acid monohydrate, 3-nitrophenylboronic acid, o-tolylboronic acid, m-tolylboronic acid, p-tolylboronic acid, 3-aminophenylboronic acid hydrochloride, π-phenylenediboronic acid, 3-chlorophenylboronic acid, 4-chlorophenylboronic acid, 4-fluorophenylboronic acid, 4-vinylphenylboronic acid, 4-methoxyphenylboronic acid, 2-formylphenylboronic acid, 4-formylphenylboronic acid, 3-(trifluoromethyl)phenylboronic acid, 4-(trifluoromethyl)phenylboronic acid, 3-bromophenylboronic acid, 3-ethoxyphenylboronic acid, 3-fluorophenylboronic acid, 3-formylphenylboronic acid, 3-iodophenylboronic acid, 3-methoxyphenylboronic acid, 2-(trifluoromethyl)phenylboronic acid, 3,5-dichlorophenylboronic acid, 2-chlorophenylboronic acid, 2-fluorophenylboronic acid, 2-methoxyphenylboronic acid, 2-ethoxyphenylboronic acid, 4-ethoxyphenylboronic acid, 3-carboxyphenylboronic acid, 4-carboxyphenylboronic acid, 4,4'-biphenyldiboronic acid, 4-(methylthio)phenylboronic acid, 2,4-difluorophenylboronic acid, 3,4-difluorophenylboronic acid, pentafluorophenylboronic acid, 2,6-difluorophenylboronic acid, 2-acetylphenylboronic acid, 3-acetylphenylboronic acid, 4-acetylphenylboronic acid, 3,5-bis(trifluoromethyl)phenylboronic acid, 3,4-dichlorophenylboronic acid, 3,5-difluorophenylboronic acid, 4-iodophenylboronic acid, 2-bromophenylboronic acid, 4-tert-butylphenylboronic acid, 2,6-dimethylphenylboronic acid, 3,5-dimethylphenylboronic acid, 2,6-dimethoxyphenylboronic acid, 3,4-dimethoxyphenylboronic acid, naphthalene-2-boronic acid, 2-naphthylboronic acid, 4-phenoxyphenylboronic acid, 4-biphenylboronic acid, 2,4-dimethoxyphenylboronic acid, 2,5-dimethoxyphenylboronic acid, 2,3-dimethylphenylboronic acid, 2,5-dimethylphenylboronic acid, 4-(dimethylamino)phenylboronic acid, 5-fluoro-2-methoxyphenylboronic acid, 4-fluoro-3-methylphenylboronic acid, 3,5-dibromophenylboronic acid, 4-ethylphenylboronic acid, 3,4-(methylenedioxy)phenylboronic acid, 3-(trifluoromethoxy)phenylboronic acid, 4-(trifluoromethoxy)phenylboronic acid, 2-fluoro-4-biphenylylboronic acid, 3-chloro-4-fluorophenylboronic acid, 5-chloro-2-methoxyphenylboronic acid, 5-formyl-2-methoxyphenylboronic acid, 2,3,4-trimethoxyphenylboronic acid, 2,5-dichlorophenylboronic acid, 4-(hydroxymethyl)phenylboronic acid, 4-borono-dl-phenylalanine, 5-bromo-2-methoxyphenylboronic acid, 2-chloro-6-methoxyphenylboronic acid, 2-fluoro-6-methoxyphenylboronic acid, 5-bromo-2-ethoxyphenylboronic acid, 3-(hydroxymethyl)phenylboronic acid, 3-formyl-4-methoxyphenylboronic acid, 3-cyanophenylboronic acid, 2,5-difluorophenylboronic acid, 2,3-difluorophenylboronic acid, 2,3-dichlorophenylboronic acid, 2-(methylthio)phenylboronic acid, 2-benzyloxyphenylboronic acid, 2,4-dichlorophenylboronic acid, 2-cyanophenylboronic acid, 4-cyanophenylboronic acid, 4-methyl-1-naphthaleneboronic acid, 4-methyl-3-nitrophenylboronic acid, 2-phenoxyphenylboronic acid, 4-butylphenylboronic acid, 4-propylphenylboronic acid, 2-ethylphenylboronic acid, 2-ethoxy-1-naphthaleneboronic acid, 6-methoxy-2-naphthaleneboronic acid, 6-ethoxy-2-naphthaleneboronic acid, 3-(trimethylsilyl)phenylboronic acid, 4-(trimethylsilyl)phenylboronic acid, 3-hydroxyphenylboronic acid, 4-hydroxyphenylboronic acid, 3-mercaptophenylboronic acid, 4-mercaptophenylboronic acid, 3-(tert-butyldimethylsilyloxy)phenylboronic acid, 2,3,4-trifluorophenylboronic acid, 2,3,6-trifluorophenylboronic acid, 2,4,6-trifluorophenylboronic acid, 2,4,5-trifluorophenylboronic acid, 2,3,5-trifluorophenylboronic acid, 3,4,5-trifluorophenylboronic acid, 4-benzoylphenylboronic acid, 3-benzyloxyphenylboronic acid, 3-biphenylboronic acid, 2-biphenylboronic acid, 3-fluoro-4-formylphenylboronic acid, 2,4,6-trimethylphenylboronic acid, 2,4,5-trimethylphenylboronic acid, 3-isopropoxyphenylboronic acid, 2-isopropoxyphenylboronic acid, 4-isopropoxyphenylboronic acid, 2-butoxyphenylboronic acid, 3-butoxyphenylboronic acid, 4-butoxyphenylboronic acid, 3-bromo-2-ethoxy-5-fluorophenylboronic acid, 5-chloro-2-ethoxyphenylboronic acid, 1-pyreneboronic acid, 4-bromo-2,6-difluorophenylboronic acid, 3-chloro-2-fluorophenylboronic acid, 5-chloro-2-fluorophenylboronic acid, 3-bromo-2,6-difluorophenylboronic acid, 2-chloro-6-fluoro-3-methylphenylboronic acid, 2-chloro-6-fluoro-5-methylphenylboronic acid, 5-chloro-2-fluoro-3-methylphenylboronic acid, 4-propoxyphenylboronic acid, 3-propoxyphenylboronic acid, 2-propoxyphenylboronic acid, 2,3-dimethoxyphenylboronic acid, 2-fluoro-5-(trifluoromethyl)phenylboronic acid, 3-bromo-2-fluorophenylboronic acid, 3-fluoro-4-methoxyphenylboronic acid, 4-ethoxy-3-fluorophenylboronic acid, 3-fluoro-4-isopropoxyphenylboronic acid, 4-butoxy-3-chlorophenylboronic acid, 3-chloro-4-isopropoxyphenylboronic acid, 3-chloro-4-propoxyphenylboronic acid, 3-chloro-4-ethoxyphenylboronic acid, 3-chloro-4-methoxyphenylboronic acid, 2-butoxy-5-fluorophenylboronic acid, 5-fluoro-2-isopropoxyphenylboronic acid, 5-methyl-2-propoxyphenylboronic acid, 4-fluoro-2-methylphenylboronic acid, 2-isopropoxy-5-methylphenylboronic acid, 2-butoxy-5-methylphenylboronic acid, 5-fluoro-2-propoxyphenylboronic acid, 4-acetamidophenylboronic acid, 4-(n-boc-amino)phenylboronic acid, 3-acetamidophenylboronic acid, 2-chloro-6-fluorophenylboronic acid, 9,9-dihexylfluorene-2,7-dioronic acid, 2-fluoro-4-methylphenylboronic acid, 3-fluoro-4-methylphenylboronic acid, 2-fluoro-5-methylphenylboronic acid, acenaphthene-5-boronic acid, 3,5-diformylphenylboronic acid, 2-ethoxy-5-methylphenylboronic acid, 2-methoxy-5-methylphenylboronic acid, 9,9-dioctylfluorene-2,7-diboronic acid, 2,3-difluoro-4-formylphenylboronic acid, 9,9-didodecylfluorene-2,7-diboronic acid, 9,9-di(2'-ethylhexyl)fluorene-2,7-diboronic acid, 4-ethoxycarbonylphenylboronic acid, 3-ethoxycarbonylphenylboronic acid, n-(4-phenylboronic)succinamic acid, 3-methoxycarbonylphenylboronic acid, 3-bromo-2-butoxyphenylboronic acid, 2,6-difluoro-4-methoxyphenylboronic acid, 2-fluoro-5-iodophenylboronic acid, 2-fluoro-3-iodophenylboronic acid, 5-bromo-2-fluorophenylboronic acid, 2-bromo-6-fluorophenylboronic acid, 4-bromo-2,3,5,6-tetrafluorophenylboronic acid, 2-fluoro-3-methoxyphenylboronic acid, 2-fluoro-3-methoxyphenylboronic acid, 2-fluoro-5-propoxyphenylboronic acid, 5-ethoxy-2-fluorophenylboronic acid, 2-ethoxy-6-fluorophenylboronic acid, 4-methoxycarbonylpheynlboronic acid, 4-butoxy-2-methylphenylboronic acid, 4-ethoxy-2-methylphenylboronic acid, 2-ethoxy-5-fluorophenylboronic acid, 4-methoxy-3-methylphenylboronic acid, 4-benzyloxy-3-chlorophenylboronic acid, 3-bromo-5-methyl-2-methoxyphenylboronic acid, 3-bromo-2-ethoxy-5-methylphenylboronic acid, 3-bromo-2-isopropoxy-5-methylphenylboronic acid, 3-bromo-5-methyl-2-propoxyphenylboronic acid, 3-bromo-2-butoxy-5-methylphenylboronic acid, 3-bromo-2-propoxyphenylboronic acid, 2-fluoro-5-methoxyphenylboronic acid, 3-bromo-2-isopropoxyphenylboronic acid, 3-(ethylthio)phenylboronic acid, 2,4-difluoro-3-formylphenylboronic acid, 4-butoxy-3,5-dimethylphenylboronic acid, 3,5-dimethyl-4-propoxyphenylboronic acid, 3,5-dimethyl-4-ethoxyphenylboronic acid, 3,5-dimethyl-4-methoxyphenylboronic acid, 3-benzyloxy-2,6-difluorophenylboronic acid, 3-(2'-chlorobenzyloxy)phenylboronic acid, 4-(3',5'-dimethoxybenzyloxy)phenylboronic acid, 3-(3',5'-dimethoxybenzyloxy)phenylboronic acid, 2-bromo-5,6-difluorophenylboronic acid, 2-fluoro-6-propoxyphenylboronic acid, 2-benzyloxy-3-bromo-5-methylphenylboronic acid, 2-(2'-chlorobenzyloxy)phenylboronic acid, 3-aminophenylboronic acid, 4-bromophenylboronic acid, 1-naphthylboronic acid, phenylboronic acid, butylboronic acid, methylboronic acid, (2-methylpropyl)boronic acid, and the corresponding boronates and boroxines thereof.

In certain embodiments, the present invention relates to the aforementioned kit, wherein said crosslinker is derived from a bis-boronic acid or a bis-boronate.

In certain embodiments, the present invention relates to the aforementioned kit, wherein said sclerosing agent is water soluble at a concentration of at least about 1 mg/mL.

In certain embodiments, the present invention relates to the aforementioned kit, wherein said sclerosing agent is water soluble at a concentration of at least about 2.5 mg/mL.

In certain embodiments, the present invention relates to the aforementioned kit, wherein said sclerosing agent is water soluble at a concentration of at least about 5 mg/mL.

In certain embodiments, the present invention relates to the aforementioned kit, wherein said sclerosing agent is water soluble at a concentration of at least about 10 mg/mL.

In certain embodiments, the present invention relates to the aforementioned kit, wherein said sclerosing agent is water soluble at a concentration of at least about 20 mg/mL.

In certain embodiments, the present invention relates to the aforementioned kit, wherein said sclerosing agent comprises a polycation.

In certain embodiments, the present invention relates to the aforementioned kit, wherein said polycation is a polyamine, a polysaccharide, or a polyamino acid.

In certain embodiments, the present invention relates to the aforementioned kit, wherein said polycation is a polysaccharide or a polyamino acid.

In certain embodiments, the present invention relates to the aforementioned kit, wherein said polycation is polylysine, polyarginine, polyornithine, chitosan polycations, gelatin polycations, or albumin polycations.

In certain embodiments, the present invention relates to the aforementioned kit, wherein said polycation is a poly(amino acid), wherein said poly(amino acid) comprises a plurality of amino acids independently selected from the group consisting of Lys and Arg; and a plurality of amino acids independently selected from the group consisting of Gly, Ala, Val, Leu, Ile, Met, Pro, Phe, Trp, Asn, Gln, Ser, Thr, Tyr, Cys, and His; provided that no less than twenty-five percent of the amino acids is independently selected from the group consisting of Lys and Arg; further provided that no more than five percent of the amino acids is independently selected from the group consisting of Asp and Glu.

In certain embodiments, the present invention relates to the aforementioned kit, wherein said polycation is a poly(amino acid), wherein said poly(amino acid) is represented by poly(X-Y), poly(X-Y-Y), or poly(X-Y-Y-Y), wherein X is independently for each occurrence Lys or Arg; and Y is independently for each occurrence Gly, Ala, Val, Leu, Ile, Met, Pro, Phe, Trp, Asn, Gln, Ser, Thr, Tyr, Cys, or His.

In certain embodiments, the present invention relates to the aforementioned kit, wherein said polycation is poly-L-lysine.

In certain embodiments, the present invention relates to the aforementioned kit, wherein said polycation degrades under physiological conditions in about 1 to about 12 weeks.

In certain embodiments, the present invention relates to the aforementioned kit, wherein said polycation degrades under physiological conditions in about 1 to about 6 weeks.

In certain embodiments, the present invention relates to the aforementioned kit, wherein said polycation degrades under physiological conditions in about 1 to about 4 weeks.

In certain embodiments, the present invention relates to the aforementioned kit, wherein said polycation degrades under physiological conditions in about 2 to about 5 weeks.

In certain embodiments, the present invention relates to the aforementioned kit, further comprising a polyanion.

In certain embodiments, the present invention relates to the aforementioned kit, wherein said polyanion is a polysaccharide or a polyamino acid.

In certain embodiments, the present invention relates to the aforementioned kit, wherein said polyanion is selected from the group consisting of sodium alginate gelatin polyanions, hyaluronic acid, carrageenan, chondroitin sulfate, carboxymethylcellulose, polyglutamic acid, and polyaspartic acid.

In certain embodiments, the present invention relates to the aforementioned kit, wherein said polyanion is chondroitin sulfate.

In certain embodiments, the present invention relates to the aforementioned kit, wherein said polyanion degrades under physiological conditions in about 1 to about 12 weeks.

In certain embodiments, the present invention relates to the aforementioned kit, wherein said polyanion degrades under physiological conditions in about 1 to about 6 weeks.

In certain embodiments, the present invention relates to the aforementioned kit, wherein said polyanion degrades under physiological conditions in about 1 to about 4 weeks.

In certain embodiments, the present invention relates to the aforementioned kit, wherein said polyanion degrades under physiological conditions in about 2 to about 5 weeks.

In certain embodiments, the present invention relates to the aforementioned kit, wherein the ratio of the product of the mass of the polycation and the charge per mass ratio of the polycation to the product of the mass of the polyanion and the charge per mass ratio of the polyanion is greater than about 1.

In certain embodiments, the present invention relates to the aforementioned kit, wherein the ratio of the product of the mass of the polycation and the charge per mass ratio of the polycation to the product of the mass of the polyanion and the charge per mass ratio of the polyanion is greater than about 1 and less than about 20.

In certain embodiments, the present invention relates to the aforementioned kit, wherein the ratio of the product of the mass of the polycation and the charge per mass ratio of the polycation to the product of the mass of the polyanion and the charge per mass ratio of the polyanion is greater than about 5 and less than about 10.

In certain embodiments, the present invention relates to the aforementioned kit, wherein the polycation and the polyanion form a precipitated complex.

In certain embodiments, the present invention relates to the aforementioned kit, wherein said sclerosing agent is a peroxide.

In certain embodiments, the present invention relates to the aforementioned kit, wherein said peroxide is hydrogen peroxide, a peroxyborate, a peroxyboric acid, a peroxycarbonate, a peroxycarbonic acid, an alkyl hydroperoxide, an aryl hydroperoxide, an aralkyl hydroperoxide, a peroxyacetate, or a peroxyacetic acid.

In certain embodiments, the present invention relates to the aforementioned kit, wherein said peroxide is sodium perborate, sodium percarbonate, or sodium peracetate.

In certain embodiments, the present invention relates to the aforementioned kit, further comprising a fourth container comprising a fifth amount of an anti-infective.

In certain embodiments, the present invention relates to the aforementioned kit, wherein said anti-infective is selected from the group consisting of an aminoglycoside, a tetracycline, a sulfonamide, p-aminobenzoic acid, a diaminopyrimidine, a quinolone, a β-lactam, a β-lactamase inhibitor, chloraphenicol, a macrolide, penicillins, cephalosporins, linomycin, clindamycin, spectinomycin, polymyxin B, colistin, vancomycin, bacitracin, isoniazid, rifampin, ethambutol, ethionamide, aminosalicylic acid, cycloserine, capreomycin, a sulfone, clofazimine, thalidomide, a polyene antifungal, flucytosine, imidazole, triazole, griseofulvin, terconazole, butoconazole ciclopirax, ciclopirox olamine, haloprogin, tolnaftate, naftifine, and terbinafine, or a combination thereof.

In certain embodiments, the present invention relates to the aforementioned kit, wherein said anti-infective is tetracycline.

In certain embodiments, the present invention relates to the aforementioned kit, further comprising a fifth container comprising a sixth amount of a contrast-enhancing agent.

In certain embodiments, the present invention relates to the aforementioned kit, wherein said contrast-enhancing agent is selected from the group consisting of radiopaque materials, paramagnetic materials, heavy atoms, transition metals, lanthanides, actinides, dyes, and radionuclide-containing materials.

SELECTED ADDITIONAL THERAPEUTIC AGENTS OF THE INVENTION. A vast number of therapeutic agents may be incorporated in the hydrogels used in the methods of the present invention. In general, therapeutic agents which may be incorporated include, without limitation: antiinfectives such as antibiotics and antiviral agents (as mentioned above); analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. Suitable pharmaceuticals for parenteral administration are well known as is exemplified by the Handbook on Injectable Drugs, 6$^{th}$ Edition, by Lawrence A. Trissel, American Society of Hospital Pharmacists, Bethesda, Md., 1990 (hereby incorporated by reference).

The pharmaceutically active compound may be any substance having biological activity, including proteins, polypeptides, polynucleotides, nucleoproteins, polysaccharides, glycoproteins, lipoproteins, and synthetic and biologically engineered analogs thereof. The term "protein" is art-recognized and for purposes of this invention also encompasses peptides. The proteins or peptides may be any biologically active protein or peptide, naturally occurring or synthetic.

Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules. The pharmaceutical agents may be selected from insulin, antigens selected from the group consisting of MMR (mumps, measles and rubella) vaccine, typhoid vaccine, hepatitis A vaccine, hepatitis B vaccine, herpes simplex virus, bacterial toxoids, cholera toxin B-subunit, influenza vaccine virus, bordetela pertussis virus, vaccinia virus, adenovirus, canary pox, polio vaccine virus, plasmodium falciparum, bacillus calmette geurin (BCG), klebsiella pneumoniae, HIV envelop glycoproteins and cytokins and other agents selected from the group consisting of bovine somatropine (sometimes referred to as BST), estrogens, androgens, insulin growth factors (sometimes referred to as IGF), interleukin I, interleukin II and cytokins. Three such cytokins are interferon-β, interferon-γ and tuftsin.

Examples of bacterial toxoids that may be incorporated in the hydrogels used in the methods of the invention are tetanus, diphtheria, pseudomonas A, mycobaeterium tuberculosis. Examples of that may be incorporated in the compositions used in the occlusion methods of the invention are HIV envelope glycoproteins, e.g., gp120 or gp 160, for AIDS vaccines. Examples of anti-ulcer H2 receptor antagonists that may be included are ranitidine, cimetidine and famotidine, and other anti-ulcer drugs are omparazide, cesupride and misoprostol. An example of a hypoglycaemic agent is glizipide.

Classes of pharmaceutically active compounds which can be loaded into that may be incorporated in the hydrogels used in the methods of the invention include, but are not limited to, anti-AIDS substances, anti-cancer substances, antibiotics, immunosuppressants (e.g., cyclosporine) anti-viral substances, enzyme inhibitors, neurotoxins, opioids, hypnotics, antihistamines, lubricants tranquilizers, anti-convulsants, muscle relaxants and anti-Parkinson substances, anti-spasmodics and muscle contractants, miotics and anti-cholinergics, anti-glaucoma compounds, anti-parasite and/or anti-protozoal compounds, anti-hypertensives, analgesics, antipyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

Exemplary pharmaceutical agents considered to be particularly suitable for incorporation in the hydrogels used in the methods of the invention include but are not limited to imidazoles, such as miconazole, econazole, terconazole, saperconazole, itraconazole, metronidazole, fluconazole, ketoconazole, and clotrimazole, luteinizing-hormone-releasing hormone (LHRH) and its analogues, nonoxynol-9, a GnRH agonist or antagonist, natural or synthetic progestrin, such as selected progesterone, 17-hydroxyprogeterone derivatives such as medroxyprogesterone acetate, and 19-nortestosterone analogues such as norethindrone, natural or synthetic estrogens, conjugated estrogens, estradiol, estropipate, and ethinyl estradiol, bisphosphonates including etidronate, alendronate, tiludronate, resedronate, clodronate, and pamidronate, calcitonin, parathyroid hormones, carbonic anhydrase inhibitor such as felbamate and dorzolamide, a mast cell stabilizer such as xesterbergsterol-A, Iodoxamine, and cromolyn, a prostaglandin inhibitor such as diclofenac and ketorolac, a steroid such as prednisolone, dexamethasone, fluoromethylone, rimexolone, and lotepednol, an antihistamine such as antazoline, pheniramine, and histiminase, pilocarpine nitrate, a beta-blocker such as levobunolol and timolol maleate. As will be understood by those skilled in the art, two or more pharmaceutical agents may be combined for specific effects. The necessary amounts of active ingredient can be determined by simple experimentation.

By way of example only, any of a number of antibiotics and antimicrobials may be included in the hydrogels used in the methods of the invention. Antimicrobial drugs preferred for inclusion in compositions used in the methods of the invention include salts of lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine and the like.

By way of example only, in the case of anti-inflammation, non-steroidal anti-inflammatory agents (NSAIDS) may be incorporated in the hydrogels used in the methods of the invention, such as propionic acid derivatives, acetic acid, fenamic acid derivatives, biphenylcarboxylic acid derivatives, oxicams, including but not limited to aspirin, acetaminophen, ibuprofen, naproxen, benoxaprofen, flurbiprofen, fenbufen, ketoprofen, indoprofen, pirprofen, carporfen, and bucloxic acid and the like.

THERAPEUTIC APPLICATIONS. In addition to being useful for treating emphysema (e.g., as described above and in the following examples), compositions of the invention may be used in other therapeutic applications.

Aspects of the invention may be used to treat any form of abnormal cellular growth (e.g., tumors, cancers, etc.) by targeting a non-toxic, yet therapeutically effective, polycationic composition to an area of diseased tissue (e.g., a tumor, adenoma, cancer, precancer, or other abnormal lesion).

Another aspect of the invention may involve the use of a polycationic hydrogel composition to treat solid organ cancer. Examples of such cancers include, but are not limited to, bronchogenic carcinoma, malignant mesothelioma, gastrointestinal cancers (e.g., esophageal cancers, rectal cancers, colon cancers), sarcomas, lipomas, fibromas, and other soft tissue cancers. Polycationic hydrogel compositions may be used to treat cancers by methods such as inducing cellular necrosis and/or microvascular thrombosis, which can result in tumor regression.

Another aspect of the invention may involve the use of a polycationic hydrogel composition to treat pleural effusions. Pleural effusions may be, for instance, ones that are refractory to medical therapy, such as malignant pleural effusions and benign, but recurrent, pleural effusions. Pleural effusions may be treated by methods such as administering a polycationic hydrogel composition within the pleural space to initiate sclerosis.

Another aspect of the invention involves the use of a polycationic hydrogel composition to treat post-operative and post traumatic wound bleeding. Wound bleeding may be treated by methods such as administering a polycationic hydrogel composition near the wound to inducing responses such as scarring.

Another aspect of the invention involves the use of a polycationic hydrogel composition to treat endoluminal bleeding. Examples of endoluminal bleeding include upper gastrointestinal bleeding from the esophagus or stomach, lower gastrointestinal bleeding from hemorrhoids or masses in the rectum or colon, and peritoneal bleeding from intraperitoneal cancers. Endoluminal bleeding may be treated by methods such as administering a polycationic hydrogel composition near and/or into the bleeding lesions to promote local microvascular thrombosis and/or rapid scar formation.

It should be appreciated that the concentration of polycations to be used can be optimized experimentally. However, the duration of exposure and the type of polycationic hydrogel composition (e.g., it's ability to induce a specific response in a targeted region) are important considerations. In one aspect, an appropriate polycation concentration may be chosen as one that results in 50% to 90% lysis (preferably about 80% lysis). The concentration required to induce lysis will depend, of course, on the type of cells in which the polycationic hydrogel compositions are exposed. Therefore, different diseases, which may occur in different regions of the body and which may be characterized by different cell types, may require different concentrations, amounts, or exposure times for one or more predetermined polycations in order to induce a desired response within a specific region of a patient. In some embodiments, the following in vitro assay can be used to determine appropriate concentrations of polycations. A flask of cells (e.g., fibroblast 3T3 cells, epithelial A549 cells, or other cells indicative of a targeted region of the body) is trypsinized and the cell suspension is split 1/10 and grown to about 80% confluence in a flask. A polycationic hydrogel composition (e.g., in the form of a solution, suspension, solid, or gel) can be added to this flask and left for about 2 minutes before being washed out. The polycation may be provided, for instance, in an isotonic salt solution. In one embodiment, the polycations are washed out (e.g., using an isotonic solution), and the percentage of lysed cells is evaluated. The cells may be stained using Trypan or another stain. The percentage of lysed cells may be calculated by comparing pictures of the flask surface (on which the cells were grown) before and after polycation exposure. The percentage lysis can be approximated by calculating the percentage of the flask surface that was cleared by the polycation. By testing different polycation concentrations, a concentration that produces the desired degree of lysis can be identified. In one embodiment, a polycationic hydrogel composition at the chosen concentration may be administered therapeutically to a targeted region in a patient (e.g., the lung) for about 2 minutes before being washed out. In one embodiment, about 10 mls of polycation composition may be delivered to a targeted region. For many polycations, a range of concentrations may be effective. For example, in certain embodiments, between 0.25% and 2% polylysine may be used. However, other concentrations also may be used (e.g., 0.1% to 5.0%). Higher or lower concentrations may be used depending on the potency of the polycation, the time of exposure to the tissue, the rate of release of the polycation, the type of disease to be treated, etc. For example, a lower concentration may be used when a more potent polycation is used or when a longer exposure time is used. Certain polycations may be more potent when they have a higher molecular weight and/or a high charge density (i.e., higher number of charged groups).

The "potency" of a compound, as used herein, refers the ability of the compound to produce a desired result in a certain group of cells or in a target region of the body. In one aspect of the invention, the potency of a polycation refers to the ability of the polycation to produce a toxic effect on cells, such as cell death. In one particular embodiment, potency may be evaluated by growing cells on gels (e.g., split a cell suspension 1/10 and lay it on a 3% fibrinogen gel) that include different concentrations of one or more polycations. In some cases, the cells are then incubated for about 72 hours. At low concentrations, a polycation may facilitate cell attachment. However, at higher concentrations, a polycation may have a toxic response, i.e., the polycation may cause cells to round up and die. According to one aspect of the invention, polycation concentrations that have a toxic response and prevent cell growth and/or cause cells to die are chosen to be included in a polycationic hydrogel composition for treating a diseased patient. The toxic response will depend, of course, on the type of cells in which the polycationic hydrogel compositions are exposed. Therefore, different diseases, which may occur in different regions of the body and which may be characterized by different cell types, may require different concentrations of polycations in order to induce a desired response within a specific region of a patient. In certain embodiments, higher molecular weight polycations may produce more toxic effects. For example, a polycationic hydrogel composition may contain PLL with a MW of between 75 and 150 kD. However, other molecular weights may be used. PLL may be toxic at 0.1%, 1% and higher concentrations in polycationic hydrogel compositions. Accordingly, in one embodiment, a polycationic hydrogel composition with 0.1%, 1%, or more PLL (or other polycation), may be used for treating a medical condition, such as emphysema. In some cases, these concentrations of polycations can be used to treat a patient without the need to use enzyme or detergent pre-treatments. In certain cases where the desired response is fibrosis, a polycationic hydrogel composition may also contain 0.1%, 1%, or more, of a polyanion, such as CS. Polyanions may act as a scaffold for fibrosis by acting as an anchor for collagen and/or fibroblasts.

EXEMPLIFICATION

The invention now being generally described, it will be more readily understood by reference to the following examples, which are included merely for purposes of illustration of certain aspects and embodiments of the present invention, and are not intended to limit the invention.

Example 1

The gelation of polyvinyl alcohol (PVA) with sodium tetraborate was investigated. A graphical depiction of this is shown in FIG. 1. Screening experiments were performed with 98-99% hydrolyzed PVA with a molecular weight ranging of 85,000 to 146,000. The initial concentration of PVA was 6% and the borate concentration was set at 100 mM for these experiments and the pH adjusted to 9 with HCl. The ratio between the two solutions was set at 9:1 (PVA:borate). The two solutions were injected through a dual lumen catheter and hydrogels were created instantaneously. The resulting hydrogels were firm and elastic. The resulting hydrogels were firm, elastic and adherent compared to fibrin hydrogels.

Example 2

A range of pH values were investigated for the borate solution as shown in Table 1 below. Experimental conditions were 6% PVA (99% hydrolyzed; molecular weight of 85,000 to 146,000), 100 mM borate, dual lumen catheter, with a 9:1 ratio of PVA to borate. Over the pH range from 8.5 to 9.5, all gels polymerized rapidly and all were firm, elastic and adherent.

TABLE 1

| pH Influence on Gel Consistency. ||
| pH Value | Gel Consistency |
| --- | --- |
| 9.5 | firm elastic gel |
| 9.25 | firm elastic gel |

TABLE 1-continued pH Influence on Gel Consistency.

| pH Value | Gel Consistency |
|---|---|
| 9 | firm elastic gel |
| 8.75 | firm elastic gel |
| 8.5 | firm elastic gel |

Example 3

The pH was set at 9 for further experiments, and the influence of PVA concentration was investigated. The results are shown in Table 2 below. Experimental conditions were PVA (99% hydrolyzed; molecular weight of 85,000 to 146,000), 100 mM borate, pH 9, dual lumen catheter, with a 9:1 ratio of PVA to borate. At concentrations of PVA below about 4%, polymer content was inadequate to produce an intact hydrogel.

TABLE 2

PVA Concentration Influence on Gel Consistency.

| PVA (99%) Concentration | Gel Consistency |
|---|---|
| 6% | firm elastic gel |
| 4% | soft elastic gel |
| 2% | slime |

Example 4

PVA with a molecular weight range of 31,000 to 50,000 was used to delineate the influence of molecular weight. The results are shown in Table 3 below. Experimental conditions were PVA (99% hydrolyzed; molecular weight of 31,000 to 50,000), 100 mM borate, pH 9, dual lumen catheter, with a 9:1 ratio of PVA to borate. When polymerized with equivalent amounts of sodium borate, lower molecular weight PVA monomers formed less firm gels than higher molecular weight PVA monomers.

TABLE 3

PVA Molecular Weight Influence on Gel Consistency.

| PVA (99%) Concentration | Gel Consistency |
|---|---|
| 6% | soft elastic gel |
| 4% | slime |
| 2% | viscosity increase |

Example 5

The influence of the hydrolysis rate of the PVA polymer was investigated by utilizing a 89% hydrolyzed PVA with a molecular weight distribution similar to the one use in the previous examples (85,000 to 124,000). The results are shown in Table 4 below. Experimental conditions were PVA (89% hydrolyzed; molecular weight of 85,000 to 124,000), 100 mM borate, pH 9, dual lumen catheter, with a 9:1 ratio of PVA to borate. Hydrolysis rate appeared to have little effect on hydrogel formation.

TABLE 4

PVA Hydrolysis Influence on Gel Consistency.

| PVA (89%) Concentration | Gel Consistency |
|---|---|
| 5% | firm elastic gel |
| 3% | soft elastic gel |
| 1.5% | viscosity increase |

Example 6

As noted above, the interaction between borate and the hydroxyl groups of the PVA polymer is pH dependent and is fully reversible by pH changes (see FIG. 1). Therefore, a PVA solution with borate can be made at acidic pH and by pH adjustment gelled to a hydrogel. A gel was instantaneously formed by mixing a 6 weight % solution of the PVA/borate with 1000 mM carbonate buffer at pH 8.6. Experimental conditions were PVA (99% hydrolyzed; molecular weight of 85,000 to 146,000), 100 mM borate, pH 5.5, dual lumen catheter, with a 8:2 ratio of PVA/borate to carbonate buffer.

Similarly, instead of sodium carbonate, 250 mM sodium phosphate buffer at pH 8.8 was used. A gel was instantaneously formed by mixing a 6 weight % solution of the PVA/borate with 250 mM phosphate buffer at pH 8.8. Experimental conditions were PVA (99% hydrolyzed; molecular weight of 85,000 to 146,000), 100 mM borate, pH 5.5, dual lumen catheter, with a 8:2 ratio of PVA/borate to phosphate buffer.

Example 7

A range of borate concentrations were investigated for the 5% PVA solution as shown in Table 5 below. Experimental conditions were 5% PVA (99% hydrolyzed; molecular weight of 85,000 to 146,000), pH=9, dual lumen catheter, with a 9:1 ratio of PVA to borate. Above about 2%, an aqueous solution of borate mixed with 5% PVA leads to rapid polymerization and formation of a firm, elastic gel.

TABLE 5

Borate Concentration Influence on Gel Consistency.

| Borate Concentration | Gel Consistency |
|---|---|
| 0.5 | Viscosity increase |
| 1 | soft elastic gel |
| 2 | firm elastic gel |
| 3 | firm elastic gel |
| 4 | firm elastic gel |

Example 8

Figure 2:
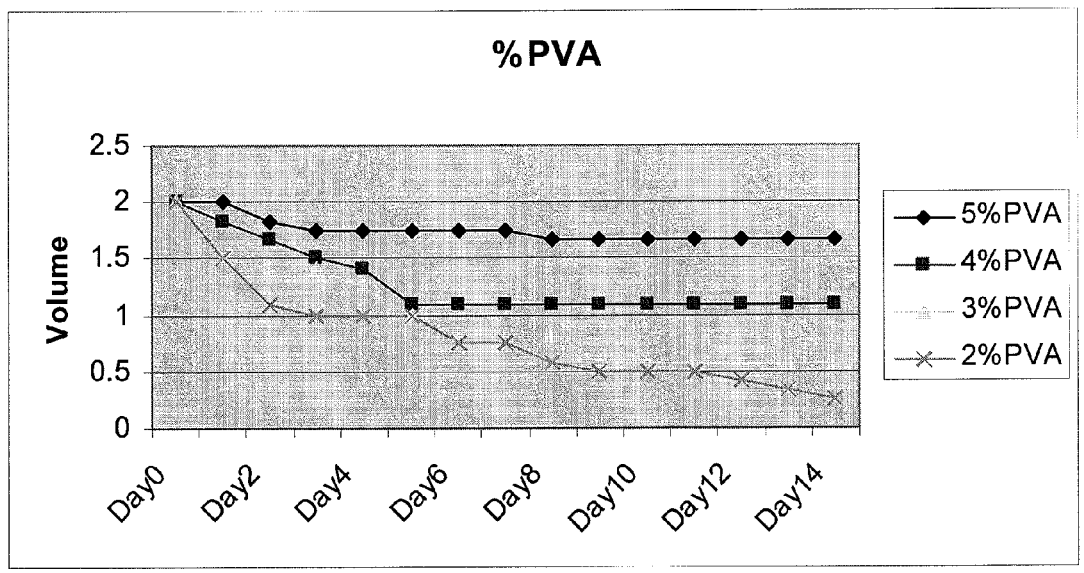
FIG. 2 depicts graphically [A] the effect of PVA concentration on hydrogel durability; and [B] the effect of additives on PVA hydrogel durability.
Figure 2:
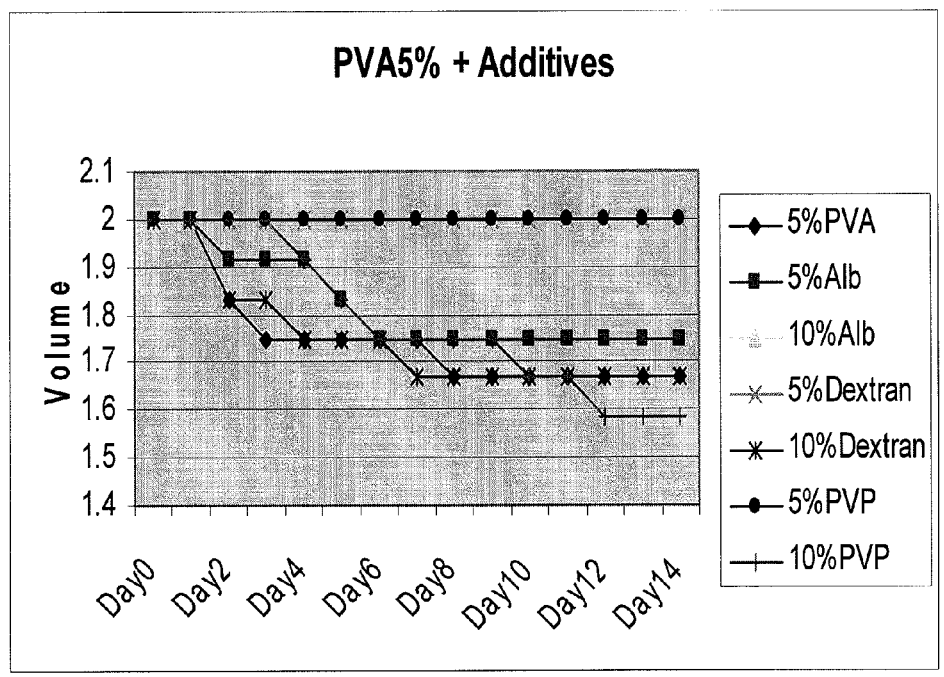

The effect of the PVA (99% hydrolysis rate; average molecular weight 100K) concentration on gel durability was evaluated by first aliquotting 0.2 mL of a 4% borate solution into bottom of 14 mL tube. Then 1.8 mL of various PVA solutions of 2-5% concentrations were added by vigorous injection through a 3 mL syringe with an 18G needle. Three tubes were prepared for of each concentration and cured at room temperature for one hour to insure complete polymerization. 8 mL of phosphate buffered saline, pH 7.4, were added to each tube, covered and incubated at room temperature. The integrity of the gels was checked by periodic inversion. The PVA hydrogel durability increases with increasing PVA concentration between 2 and 5% as shown in the graph in FIG. 2[A].

Example 9

The effect of additives on the durability of the PVA gel (99% hydrolysis rate; average molecular weight 100K) was evaluated by first aliquotting 0.2 mL of a 4% borate solution into bottom of 14 mL tube. See FIG. 2B. Then 1.8 mL of PVA (5%) and additive containing solutions of 2-5% concentrations were added by vigorous injection through a 3 mL syringe with an 18G needle. Three tubes were prepared for of each concentration and cured at room temperature for one hour to insure complete polymerization. 8 mL of phosphate buffered saline, pH 7.4, were added to each tube, covered and incubated at room temperature. The integrity of the gels was checked by periodic inversion.

The additives investigated were: 5 & 10% albumin, 5 & 10% PVP (polyvinylpyrolidone, (MW 55K), 5 & 10% dextran (MW 100K).

10% albumin, 5% dextran, and 5% PVP increase the durability of 5% PVA hydrogels, while the other concentrations investigated had less pronounced effects on the durability.

Example 10

Figure 3:
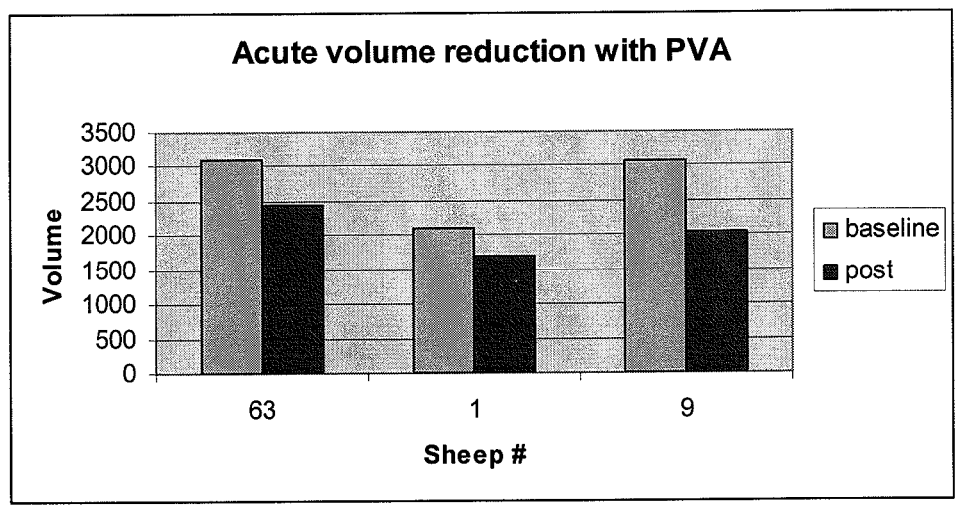
FIG. 3 depicts graphically results from experiments in sheep assessing the efficacy of various PVA mixtures in lung volume reduction.
Figure 3:
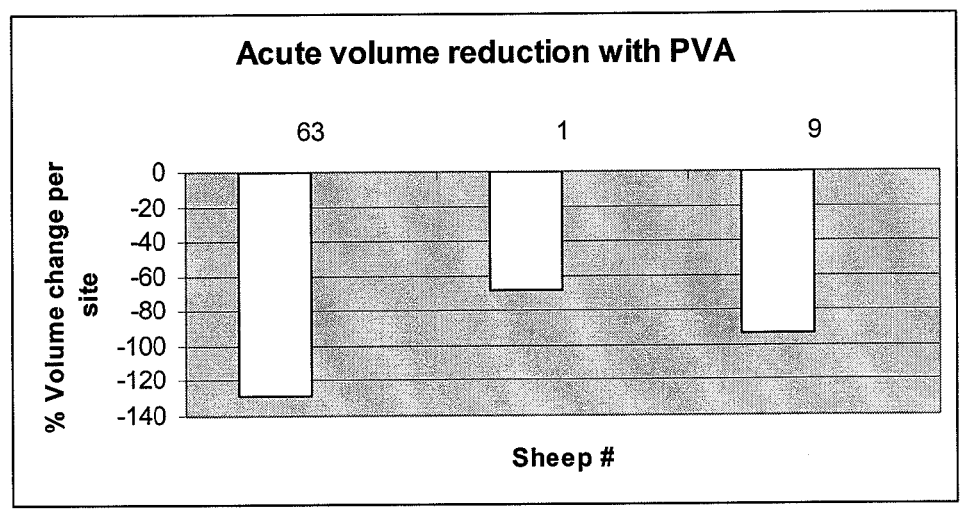

See FIGS. 3[A] and 3[B]. Three sheep were treated with PVA mixtures to assess their ability to reduce lung volume. The first sheep (sheep #63) was treated with a mixture containing 5% PVA, 0.5% chondroitin sulfate, 0.5% poly-L-lysine, and 0.5% tetracycline, polymerized with a solution containing 4% sodium borate decahydrate and 1 M Tris pH 8.5. The sheep was anesthetized, intubated, and mechanically ventilated. A baseline CT scan was obtained at 25 cm $H_2O$ transpulmonary pressure. A 5 mm endoscope passed into wedge position at a subsegmental target site. A dual lumen catheter was passed through the working channel into the target site approximately 2 cm past the tip of the endoscope. 5-10 mL of the PVA Solution was mixed with 10-15 mL O2 via a 3-way stopcock to generate 20 mL of foam and then simultaneously injected with 3 mL Borate Solution via the dual lumen catheter. The catheter and endoscope were removed and repositioned at the next target site. Five total sites were treated. Immediately post treatment, repeat CT scan showed dramatic volume reduction despite the limited number of treatment sites. Volume integration revealed volume reduction of 129 mL (4.2%) per site for a total of 21% volume reduction. Follow-up CT scans and necropsy at 1 week showed sustained volume reduction with evidence of early scar formation at treatment sites.

A second sheep (sheep #1) was treated with a mixture containing 4% PVA, 0.5% chondroitin sulfate, 0.5% poly-L-lysine, 1% tyloxapol (v/v), and 5% polyvinyl pyrrolidine (PVP), polymerized with a solution containing 4% sodium borate decahydrate and 1 M Tris pH 8.5. The sheep was anesthetized, intubated, and mechanically ventilated. A baseline CT scan was obtained at 25 cm $H_2O$ transpulmonary pressure. An 8 mm endoscope passed into wedge position at a segmental target site. A dual lumen catheter was passed through the working channel into the target site approximately 2 cm past the tip of the endoscope. Five mL of the PVA Solution was mixed with 5 mL $O_2$ via a 3-way stopcock to generate 10 mL of foam, then injected through the large lumen of the catheter. Next, another 5 mL of PVA solution was mixed with 5 mL of $O_2$ and injected simultaneously with 1.5 mL Borate via the dual lumen catheter. Finally, 1.5 mL of Borate was injected via the small lumen of the catheter. The catheter and endoscope were removed and repositioned at the next target site. Six sites were treated. Post-treatment CT scans showed significant acute volume reduction. Volume integration revealed volume reduction of 68.3 mL (3.3%) per site for a total of 19.8% volume reduction. Necropsy at 1 week showed sustained volume reduction at treatment sites.

A third sheep (sheep #9) was treated with a mixture containing 4% PVA, 0.5% chondroitin sulfate, 0.5% poly-L-lysine, 5% polyvinylpyrrolidine, and 150 mM Tris pH 8.5, polymerized with a solution containing 4% sodium borate decahydrate and 1 M Tris pH 8.5. The sheep was anesthetized, intubated, and mechanically ventilated. A baseline CT scan was performed at 25 cm $H_2O$ transpulmonary pressure. An 8 mm endoscope passed into wedge position at a segmental target site. A dual lumen catheter was passed through the working channel into the target site approximately 2 cm past the tip of the endoscope. PVA and Borate solutions were injected simultaneously through the catheter using the hand-held device. The PVA solution was administered as a gel rather than a foam. The catheter was removed and 30-60 mL of air was injected through the working channel of the endoscope. After 60-120 seconds, the endoscope was removed and repositioned at the next target site. Twelve sites were treated. Post-treatment CT scans showed variable infiltrates that generally appeared more focal compared with prior foam treatments. Volume integration revealed volume reduction of 93.7 mL (3.1%) per site for a total of 37.2% volume reduction.

Example 11

A 2% solution of sodium perborate was prepared and used for crosslinking a 6% PVA solution. A firm, elastic gel was instantaneously formed by mixing the two solutions. Experimental conditions were 6% PVA (99% hydrolyzed; molecular weight of 85,000 to 146,000), pH=9, dual lumen catheter, with a 9:1 ratio of PVA to perborate).

Example 12

A 2% solution of sodium perborate was prepared and 100 mM sodium percarbonate was added. This solution was used for crosslinking a 6% PVA solution. A firm, elastic gel was instantaneously formed by mixing the two solutions. Experimental conditions were 6% PVA (99% hydrolyzed; molecular weight of 85,000 to 146,000), pH=9.5, dual lumen catheter, with a 9:1 ratio of PVA to perborate, 100 mM sodium percarbonate).

Example 13

A 2% solution of sodium perborate was prepared and 10 mg/mL solid benzoylperoxide was added. This solution was used for crosslinking a 6% PVA solution. A firm, elastic gel was instantaneously formed by mixing the two solutions. Experimental conditions were 6% PVA (99% hydrolyzed; molecular weight of 85,000 to 146,000), pH=9, 9:1 ratio of PVA to perborate, 10 mg/mL benzoylperoxide).

Example 14

A 2% solution of sodium perborate was prepared and 3% hydrogen peroxide was added. This solution was used for crosslinking a 6% PVA solution. A firm, elastic gel was instantaneously formed by mixing the two solutions. Experimental conditions were 6% PVA (99% hydrolyzed; molecular weight of 85,000 to 146,000), pH=9, 9:1 ratio of PVA to perborate, 3% hydrogen peroxide).

Example 15

A 3% solution of sodium borate was prepared and 3% hydrogen peroxide was added. This solution was used for crosslinking a 6% PVA solution. A firm, elastic gel was instantaneously formed by mixing the two solutions. Experimental conditions were 6% PVA (99% hydrolyzed; molecular weight of 85,000 to 146,000), pH=9, 9:1 ratio of PVA to borate, 3% hydrogen peroxide).

INCORPORATION BY REFERENCE

U.S. Pat. No. 6,610,043 is hereby incorporated by reference in its entirety. U.S. Pat. No. 6,709,401 is hereby incorporated by reference in its entirety. U.S. Pat. No. 6,682,520 is hereby incorporated by reference in its entirety. US Patent Application 2002/0147462 is hereby incorporated by reference in its entirety. US Patent Application 2003/0018351 is hereby incorporated by reference in its entirety. US Patent Application 2003/0228344 is hereby incorporated by reference in its entirety. US Patent Application 2004/0200484 is hereby incorporated by reference in its entirety. US Patent Application 2004/0038868 is hereby incorporated by reference in its entirety. US Patent Application 2005/0239685 is hereby incorporated by reference in its entirety. In addition, all of the US Patents and US Published Patent Applications cited herein are hereby incorporated by reference.

EQUIVALENTS while Several Embodiments of the Present Invention are Described and Illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

We claim:

1. A method for reducing lung volume in a patient, comprising the steps of:

advancing into a region of a patient's lung via said patient's trachea a multi-lumen catheter lumen through a bronchoscope; and co-administering, through the multi-lumen catheter, a first mixture comprising a first amount of a polymer containing a plurality of pendent hydroxyl groups; a second mixture comprising a second amount of a crosslinker; and a third mixture comprising a third amount of a sclerosing agent; thereby forming a hydrogel in said region, wherein said crosslinker is derived from compounds selected from the group consisting of boric acid, sodium borate, potassium borate, alkyl boronic acids, alkyl boronates, alkyl boroxine, alkenyl boronic acids, alkenyl boronates, alkenyl boroxine, aryl boronic acids, aryl boronates, aryl boroxine, heteroaryl boronic acids, heteroaryl boronates, heteroaryl boroxine, aralkyl boronic acid, aralkyl boronates, aralkyl boroxine, heteroaralkyl boronic acids, heteroaralkyl boronates and heteroaralkyl boroxine; and said polymer is polyvinyl alcohol or a copolymer of vinyl alcohol and a second monomer.

2. The method of claim 1, wherein said polymer is copolymer of vinyl alcohol and a second monomer; wherein said second monomer is selected from the group consisting of olefins, propylene, 1-butene, isobutene, acrylic acid, acrylic acid salts, acrylates, methyl acrylate, ethyl acrylate, n-propyl acrylate, i-propyl acrylate, n-butyl acrylate, i-butyl acrylate, t-butyl acrylate, 2-ethylhexyl acrylate, dodecyl acrylate, octadecyl acrylate, methacrylic acid, methacrylic acid salts, methacrylates, methyl methacrylate, ethyl methacrylate, n-propyl methacrylate, i-propyl methacrylate, n-butyl methacrylate, i-butyl methacrylate, t-butyl methacrylate, 2-ethylhexyl methacrylate, dodecyl methacrylate, octadecyl methacrylate, acrylamide, N-methylacrylamide, N-ethylacrylamide, N,N-dimethylacrylamide, diacetonacrylamide, acrylamidopropanesulfonic acid, salts of acrylamidopropanesulfonic acid, acrylamidopropyldimethylamine, salts of acrylamidopropyldimethylamine, N-methylolacrylamide, methacrylamide, N-methylmethacrylamide, N-ethylmethacrylamide, methacrylamidopropanesulfonic acid, salts of methacrylamidopropanesulfonic acid, methacrylamidopropyldimethylamine, salts of methacrylamidopropyldimethylamine, N-methylolmethacrylamide, N-vinylamides, N-vinylformamide, N-vinylacetamide, N-vinylpyrrolidone, vinyl ethers, methyl vinyl ether, ethyl vinyl ether, n-propyl vinyl ether, i-propyl vinyl ether, n-butyl vinyl ether, i-butyl vinyl ether, t-butyl vinyl ether, dodecyl vinyl ether, stearyl vinyl ether, nitriles, acrylonitrile, methacrylonitrile, vinyl halides, vinyl chloride, vinylidene chloride, vinyl fluoride, vinylidene fluoride, allyl compounds, allyl acetate, allyl chloride, maleic acid, salts of maleic acid, maleic acid esters, itaconic acid, salts of itaconic acid, itaconic acid esters, vinylsilyl compounds, vinyltrimethoxysilane, isopropenyl acetate, N-vinylamides, N-vinylformamide, N-vinylacetamide, and N-vinylpyrrolidone.

3. The method of claim 2, wherein said copolymer is a block copolymer, random copolymer, graft polymer, or branched copolymer.

4. The method of claim 1, wherein said crosslinker is derived from an optionally-substituted phenyl boronic acid, an optionally-substituted phenyl boronate, or an optionally-substituted phenyl boroxine.

5. The method of claim 1, wherein said crosslinker is derived from compounds selected from the group consisting of trans-2-phenylvinylboronic acid, trans-2-(4-chlorophenyl)vinylboronic acid, trans-2-(4-fluorophenyl)vinylboronic acid, trans-2-(4-methoxyphenyl)vinylboronic acid, trans-2-(4-(trifluoromethyl)phenyl)vinylboronic acid, trans-1-hexen-1-ylboronic acid, trans-1-octen-1-ylboronic acid, trans-2-[3-(trifluoromethyl)phenyl]vinylboronic acid, trans- 2-(4-biphenyl)vinylboronic acid, trans-2-(3-methoxyphenyl)vinylboronic acid, trans-2-chloromethylvinylboronic acid, (ε)-5-chloro-1-penteneboronic acid, trans-2-(4-methylphenyl)vinylboronic acid, α-phenyl vinylboronic acid, cis-propenylboronic acid, trans-propenylboronic acid, 1-pentenylboronic acid, 2-cyclohexylvinylboronic acid, 1-benzothiophen-2-ylboronic acid, n-boc-2-pyrryl-boronic acid, 2-thienylboronic acid, thiophene-3-boronic acid, 2-furanboronic acid, 2,5-thiophenediboronic acid, 2-formyl-3-thiopheneboronic acid, 3-formyl-2-thiopheneboronic acid, 5-acetyl-2-thiopheneboronic acid, 5-chloro-2-thienylboronic acid, benzofuran-2-ylboronic acid, 4-dibenzofuranboronic acid, benzothiophen-2-ylboronic acid, 4-dibenzothiopheneboronic acid, thianaphthene-3-boronic acid, 3-pyridineboronic acid, 3-furanboronic acid, 5-methyl-2-thiopheneboronic acid, thianthrene-1-boronic acid, 5-methyl-2-furanboronic acid, 5-formyl-2-furanboronic acid, 5-formyl-2-thiopheneboronic acid, 4-methyl-3-thiopheneboronic acid, 5-bromothiophene-2-boronic acid, N-Boc-indole-2-boronic acid, 1-(phenylsulfonyl)-2-indoleboronic acid, 1-(phenylsulfonyl)-3-indoleboronic acid, 4-pyridineboronic acid, 2-chloro-5-pyridineboronic acid, 3-aminophenylboronic acid monohydrate, 3-nitrophenylboronic acid, o-tolylboronic acid, m-tolylboronic acid, p-tolylboronic acid, 3-aminophenylboronic acid hydrochloride, π-phenylenediboronic acid, 3-chlorophenylboronic acid, 4-chlorophenylboronic acid, 4-fluorophenylboronic acid, 4-vinylphenylboronic acid, 4-methoxyphenylboronic acid, 2-formylphenylboronic acid, 4-formylphenylboronic acid, 3-(trifluoromethyl)phenylboronic acid, 4-(trifluoromethyl)phenylboronic acid, 3-bromophenylboronic acid, 3-ethoxyphenylboronic acid, 3-fluorophenylboronic acid, 3-formylphenylboronic acid, 3-iodophenylboronic acid, 3-methoxyphenylboronic acid, 2-(trifluoromethyl)phenylboronic acid, 3,5-dichlorophenylboronic acid, 2-chlorophenylboronic acid, 2-fluorophenylboronic acid, 2-methoxyphenylboronic acid, 2-ethoxyphenylboronic acid, 4-ethoxyphenylboronic acid, 3-carboxyphenylboronic acid, 4-carboxyphenylboronic acid, 4,4'-biphenyldiboronic acid, 4-(methylthio)phenylboronic acid, 2,4-difluorophenylboronic acid, 3,4-difluorophenylboronic acid, pentafluorophenylboronic acid, 2,6-difluorophenylboronic acid, 2-acetylphenylboronic acid, 3-acetylphenylboronic acid, 4-acetylphenylboronic acid, 3,5-bis(trifluoromethyl)phenylboronic acid, 3,4-dichlorophenylboronic acid, 3,5-difluorophenylboronic acid, 4-iodophenylboronic acid, 2-bromophenylboronic acid, 4-tert-butylphenylboronic acid, 2,6-dimethylphenylboronic acid, 3,5-dimethylphenylboronic acid, 2,6-dimethoxyphenylboronic acid, 3,4-dimethoxyphenylboronic acid, naphthalene-2-boronic acid, 2-naphthylboronic acid, 4-phenoxyphenylboronic acid, 4-biphenylboronic acid, 2,4-dimethoxyphenylboronic acid, 2,5-dimethoxyphenylboronic acid, 2,3-dimethylphenylboronic acid, 2,5-dimethylphenylboronic acid, 4-(dimethylamino)phenylboronic acid, 5-fluoro-2-methoxyphenylboronic acid, 4-fluoro-3-methylphenylboronic acid, 3,5-dibromophenylboronic acid, 4-ethylphenylboronic acid, 3,4-(methylenedioxy)phenylboronic acid, 3-(trifluoromethoxy)phenylboronic acid, 4-(trifluoromethoxy)phenylboronic acid, 2-fluoro-4-biphenylylboronic acid, 3-chloro-4-fluorophenylboronic acid, 5-chloro-2-methoxyphenylboronic acid, 5-formyl-2-methoxyphenylboronic acid, 2,3,4-trimethoxyphenylboronic acid, 2,5-dichlorophenylboronic acid, 4-(hydroxymethyl)phenylboronic acid, 4-borono-dl-phenylalanine, 5-bromo-2-methoxyphenylboronic acid, 2-chloro-6-methoxyphenylboronic acid, 2-fluoro-6-methoxyphenylboronic acid, 5-bromo-2-ethoxyphenylboronic acid, 3-(hydroxymethyl)phenylboronic acid, 3-formyl-4-methoxyphenylboronic acid, 3-cyanophenylboronic acid, 2,5-difluorophenylboronic acid, 2,3-difluorophenylboronic acid, 2,3-dichlorophenylboronic acid, 2-(methylthio)phenylboronic acid, 2-benzyloxyphenylboronic acid, 2,4-dichlorophenylboronic acid, 2-cyanophenylboronic acid, 4-cyanophenylboronic acid, 4-methyl-1-naphthaleneboronic acid, 4-methyl-3-nitrophenylboronic acid, 2-phenoxyphenylboronic acid, 4-butylphenylboronic acid, 4-propylphenylboronic acid, 2-ethylphenylboronic acid, 2-ethoxy-1-naphthaleneboronic acid, 6-methoxy-2-naphthaleneboronic acid, 6-ethoxy-2-naphthaleneboronic acid, 3-(trimethylsilyl)phenylboronic acid, 4-(trimethylsilyl)phenylboronic acid, 3-hydroxyphenylboronic acid, 4-hydroxyphenylboronic acid, 3-mercaptophenylboronic acid, 4-mercaptophenylboronic acid, 3-(tert-butyldimethylsilyoxy)phenylboronic acid, 2,3,4-trifluorophenylboronic acid, 2,3,6-trifluorophenylboronic acid, 2,4,6-trifluorophenylboronic acid, 2,4,5-trifluorophenylboronic acid, 2,3,5-trifluorophenylboronic acid, 3,4,5-trifluorophenylboronic acid, 4-benzoylphenylboronic acid, 3-benzyloxyphenylboronic acid, 3-biphenylboronic acid, 2-biphenylboronic acid, 3-fluoro-4-formylphenylboronic acid, 2,4,6-trimethylphenylboronic acid, 2,4,5-trimethylphenylboronic acid, 3-isopropoxyphenylboronic acid, 2-isopropoxyphenylboronic acid, 4-isopropoxyphenylboronic acid, 2-butoxyphenylboronic acid, 3-butoxyphenylboronic acid, 4-butoxyphenylboronic acid, 3-bromo-2-ethoxy-5-fluorophenylboronic acid, 5-chloro-2-ethoxyphenylboronic acid, 1-pyreneboronic acid, 4-bromo-2,6-difluorophenylboronic acid, 3-chloro-2-fluorophenylboronic acid, 5-chloro-2-fluorophenylboronic acid, 3-bromo-2,6-difluorophenylboronic acid, 2-chloro-6-fluoro-3-methylphenylboronic acid, 2-chloro-6-fluoro-5-methylphenylboronic acid, 5-chloro-2-fluoro-3-methylphenylboronic acid, 4-propoxyphenylboronic acid, 3-propoxyphenylboronic acid, 2-propoxyphenylboronic acid, 2,3-dimethoxyphenylboronic acid, 2-fluoro-5-(trifluoromethyl)phenylboronic acid, 3-bromo-2-fluorophenylboronic acid, 3-fluoro-4-methoxyphenylboronic acid, 4-ethoxy-3-fluorophenylboronic acid, 3-fluoro-4-isopropoxyphenylboronic acid, 4-butoxy-3-chlorophenylboronic acid, 3-chloro-4-isopropoxyphenylboronic acid, 3-chloro-4-propoxyphenylboronic acid, 3-chloro-4-ethoxyphenylboronic acid, 3-chloro-4-methoxyphenylboronic acid, 2-butoxy-5-fluorophenylboronic acid, 5-fluoro-2-isopropoxyphenylboronic acid, 5-methyl-2-propoxyphenylboronic acid, 4-fluoro-2-methylphenylboronic acid, 2-isopropoxy-5-methylphenylboronic acid, 2-butoxy-5-methylphenylboronic acid, 5-fluoro-2-propoxyphenylboronic acid, 4-acetamidophenylboronic acid, 4-(n-boc-amino)phenylboronic acid, 3-acetamidophenylboronic acid, 2-chloro-6-fluorophenylboronic acid, 9,9-dihexylfluorene-2,7-dioronic acid, 2-fluoro-4-methylphenylboronic acid, 3-fluoro-4-methylphenylboronic acid, 2-fluoro-5-methylphenylboronic acid, acenaphthene-5-boronic acid, 3,5-diformylphenylboronic acid, 2-ethoxy-5-methylphenylboronic acid, 2-methoxy-5-methylphenylboronic acid, 9,9-dioctylfluorene-2,7-diboronic acid, 2,3-difluoro-4-formylphenylboronic acid, 9,9-didodecylfluorene-2,7-diboronic acid, 9,9-di(2'-ethylhexyl)fluorene-2,7-diboronic acid, 4-ethoxycarbonylphenylboronic acid, 3-ethoxycarbonylphenylboronic acid, n-(4-phenylboronic)succinamic acid, 3-methoxycarbonylphenylboronic acid, 3-bromo-2-butoxyphenylboronic acid, 2,6-difluoro-4-methoxyphenylboronic acid, 2-fluoro-5-iodophenylboronic acid, 2-fluoro-3-iodophenylboronic acid, 5-bromo-2-fluorophenylboronic acid, 2-bromo-6-fluorophenylboronic acid, 4-bromo-2,3,5,6-tetrafluorophenylboronic acid, 2-fluoro-3-methoxyphenylboronic acid, 2-fluoro-3-methoxyphenylboronic acid, 2-fluoro-5-propoxyphenylboronic acid, 5-ethoxy-2-fluorophenylboronic acid, 2-ethoxy-6-fluorophenylboronic acid, 4-methoxycarbonylpheynlboronic acid, 4-butoxy-2-methylphenylboronic acid, 4-ethoxy-2-methylphenylboronic acid, 2-ethoxy-5-fluorophenylboronic acid, 4-methoxy-3-methylphenylboronic acid, 4-benzyloxy-3-chlorophenylboronic acid, 3-bromo-5-methyl-2-methoxyphenylboronic acid, 3-bromo-2-ethoxy-5-methylphenylboronic acid, 3-bromo-2-isopropoxy-5-methylphenylboronic acid, 3-bromo-5-methyl-2-propoxyphenylboronic acid, 3-bromo-2-butoxy-5-methylphenylboronic acid, 3-bromo-2-propoxyphenylboronic acid, 2-fluoro-5-methoxyphenylboronic acid, 3-bromo-2-isopropoxyphenylboronic acid, 3-(ethylthio)phenylboronic acid, 2,4-difluoro-3-formylphenylboronic acid, 4-butoxy-3,5-dimethylphenylboronic acid, 3,5-dimethyl-4-propoxyphenylboronic acid, 3,5-dimethyl-4-ethoxyphenylboronic acid, 3,5-dimethyl-4-methoxyphenylboronic acid, 3-benzyloxy-2,6-difluorophenylboronic acid, 3-(2'-chlorobenzyloxy)phenylboronic acid, 4-(3',5'-dimethoxybenzyloxy)phenylboronic acid, 3-(3',5'-dimethoxybenzyloxy)phenylboronic acid, 2-bromo-5,6-difluorophenylboronic acid, 2-fluoro-6-propoxyphenylboronic acid, 2-benzyloxy-3-bromo-5-methylphenylboronic acid, 2-(2'-chlorobenzyloxy)phenylboronic acid, 3-aminophenylboronic acid, 4-bromophenylboronic acid, 1-naphthylboronic acid, phenylboronic acid, butylboronic acid, methylboronic acid, (2-methylpropyl)boronic acid, and the corresponding boronates and boroxines thereof.

6. The method of claim 1, wherein said sclerosing agent comprises a polycation; said polycation is a poly(amino acid); and said poly(amino acid) comprises a plurality of amino acids independently selected from the group consisting of Lys and Arg; and a plurality of amino acids independently selected from the group consisting of Gly, Ala, Val, Leu, Ile, Met, Pro, Phe, Trp, Asn, Gln, Ser, Thr, Tyr, Cys, and His; provided that no less than twenty-five percent of the amino acids is independently selected from the group consisting of Lys and Arg; further provided that no more than five percent of the amino acids is independently selected from the group consisting of Asp and Glu.

7. The method of claim 1, wherein said sclerosing agent comprises a polycation; said polycation is a poly(amino acid); said poly(amino acid) is represented by poly(X-Y), poly(X-Y-Y), or poly(X-Y-Y-Y); X is independently for each occurrence Lys or Arg; and Y is independently for each occurrence Gly, Ala, Val, Leu, Ile, Met, Pro, Phe, Trp, Asn, Gln, Ser, Thr, Tyr, Cys, or His.

8. The method of claim 1, wherein the third mixture further comprises a fourth amount of a polyanion; and the sclerosing agent comprises a polycation.

9. The method of claim 1, wherein said sclerosing agent is a peroxide.

10. The method of claim 9, wherein said peroxide is hydrogen peroxide, a peroxyborate, a peroxyboric acid, a peroxycarbonate, a peroxycarbonic acid, an alkyl hydroperoxide, an aryl hydroperoxide, an aralkyl hydroperoxide, a peroxyacetate, or a peroxyacetic acid.

11. The method of claim 9, wherein said peroxide is sodium perborate, sodium percarbonate, or sodium peracetate.

12. The method of claim 1, further comprising the step of co-administering to said patient a contrast-enhancing agent.

13. The method of claim 12, wherein said contrast-enhancing agent is selected from the group consisting of radiopaque materials, paramagnetic materials, heavy atoms, transition metals, lanthanides, actinides, dyes, and radionuclide-containing materials.

14. The method of claim 1, wherein the sclerosing agent is polylysine.

15. The method of claim 1, wherein the sclerosing agent is poly(l-lysine).

* * * * *

UNITED STATES PATENT AND TRADEMARK OFFICE
CERTIFICATE OF CORRECTION

PATENT NO. : 8,361,484 B2
APPLICATION NO. : 12/443021
DATED : January 29, 2013
INVENTOR(S) : Edward P. Ingenito et al.

Page 1 of 1

It is certified that error appears in the above-identified patent and that said Letters Patent is hereby corrected as shown below:

On the Title Sheet:

At field number (73) Assignee: replace:

"Aeris Therapeutics, Inc." with

--Aeris Therapeutics, LLC--

At field number (22) PCT Filed: replace:

"Sep. 27, 2007" with

--Sep. 26, 2007--

Signed and Sealed this
Second Day of April, 2013

Teresa Stanek Rea
*Acting Director of the United States Patent and Trademark Office*